US011969396B2

(12) United States Patent
Rammohan Shenoy et al.

(10) Patent No.: US 11,969,396 B2
(45) Date of Patent: *Apr. 30, 2024

(54) IPA-3-LOADED LIPOSOMES AND METHODS OF USE THEREOF

(71) Applicant: University of Georgia Research Foundation, Inc., Hall Athens, GA (US)

(72) Inventors: Somanath Rammohan Shenoy, Martinez, GA (US); Brian S. Cummings, Athens, GA (US); Wided Najahi-Missaoui, Athens, GA (US)

(73) Assignee: UNIVERSITY OF GEORGIA RESEARCH FOUNDATION, INC., Athens, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/047,915

(22) Filed: Oct. 19, 2022

(65) Prior Publication Data

US 2023/0110087 A1    Apr. 13, 2023

Related U.S. Application Data

(63) Continuation of application No. 16/077,980, filed as application No. PCT/US2017/017828 on Feb. 14, 2017, now Pat. No. 11,517,539.

(Continued)

(51) Int. Cl.
*A61K 31/105* (2006.01)
*A61K 9/127* (2006.01)
*A61P 35/00* (2006.01)

(52) U.S. Cl.
CPC .......... *A61K 31/105* (2013.01); *A61K 9/1271* (2013.01); *A61K 9/1275* (2013.01); *A61P 35/00* (2018.01)

(58) Field of Classification Search
CPC .................................................. A61K 9/1271
See application file for complete search history.

(56) References Cited

U.S. PATENT DOCUMENTS 8,329,213 B2   12/2012   Hong
8,709,379 B2    4/2014   Parchment
(Continued)

FOREIGN PATENT DOCUMENTS

| WO | 2012065935 | 5/2012 |
|----|------------|--------|
| WO | 2015105484 | 7/2015 |
| WO | 2015148985 | 10/2015 |

OTHER PUBLICATIONS

Allen et al.(Bioscience Reports, vol. 22, No. 2, Apr. 2002, 225-250) . (Year: 2002).*

(Continued)

*Primary Examiner* — Benjamin J Packard
(74) *Attorney, Agent, or Firm* — PABST PATENT GROUP LLP

(57) ABSTRACT

Lipid-based delivery vehicles are provided. Nanoparticulate compositions typically including a p21 activated kinase (PAK) inhibitor and a lipid-based delivery vehicle are also provided. In preferred embodiments, the lipid-based delivery vehicle is a liposome, most preferably a sterically-stabilized liposome. Typically the lipid-based delivery vehicle includes one or more phospholipids, and optionally a sterol. In some embodiments, at least one of the phospholipids is PEGylated. In particular embodiments, the lipid-based delivery vehicle includes DSPC, DSPE-PEG2000, and cholesterol. In specific embodiments, the ratio of DSPC, DSPE-PEG, and cholesterol is 9:1:5. The nanoparticulate composition typically includes a PAK inhibitor, preferably a PAK-1 inhibitor such as IPA-3 or a derivative, prodrug, or pharmaceutically acceptable salt thereof. Methods of use, for example methods of treating cancer, particularly prostate (Continued)

and breast cancer by administering the composition to subjects in need thereof, are also provided.

20 Claims, 9 Drawing Sheets

Related U.S. Application Data

(60) Provisional application No. 62/295,331, filed on Feb. 15, 2016.

(56) References Cited

U.S. PATENT DOCUMENTS

| | | | |
|---|---|---|---|
| 8,771,682 | B2 | 7/2014 | Bökel |
| 9,789,193 | B2 | 10/2017 | Sengupta |
| 10,058,507 | B2 | 8/2018 | Tardi |
| 10,071,056 | B2 | 9/2018 | Zale |
| 10,213,385 | B2 | 2/2019 | Yang |
| 11,045,554 | B1 | 6/2021 | Negrete |
| 11,219,634 | B2 | 1/2022 | Prieve |
| 2004/0102623 | A1 | 5/2004 | Monia |
| 2007/0116753 | A1 | 5/2007 | Hong |
| 2008/0097062 | A1 | 4/2008 | Zhao |
| 2012/0231069 | A1 | 9/2012 | Nowotnik |
| 2013/0022665 | A1 | 1/2013 | Niitsu |
| 2013/0059824 | A1 | 3/2013 | Lichter |
| 2014/0154264 | A1 | 6/2014 | Cheresh |
| 2014/0271821 | A1 | 9/2014 | Mcghee |
| 2015/0359815 | A1 | 12/2015 | Steidl |
| 2016/0030341 | A1 | 2/2016 | Hong |
| 2017/0112800 | A1 | 4/2017 | Roy |
| 2019/0151461 | A1 | 5/2019 | Brown |

OTHER PUBLICATIONS

Lap-Yan Wong et al.(PLOS One, 2013, V 8 1 7, e68843). (Year: 2013).*

Haeri, et al., "Preparation and characterization of stable nanoliposomal formulation of fluoxetine as a potential adjuvant therapy for drug-resistant tumors" Iranian journal of pharmaceutical research, 1-14 (2014).

Wong, et al., "An investigation on p21-activated protein kinase 1 inhibitor, IPA-3, in hepatocellular carcinoma" Cancer Research 72(8 Suppl): Abstract nr 4429 (2012).

Al-Azayzih, et al., "P21 activated kinase-1 mediates transforming growth factor β1-induced prostate cancer cell epithelial to mesenchymal transition", Biochim. Biophys. Acta., 1853(5):1229-39 (2015).

Allen, et al., "Liposomes containing synthetic lipid derivatives of poly(ethylene glycol) show prolonged circulation half-lives in vivo", Biochim. Biophys. Acta., 1066(1):29-36 (1991).

Briuglia, et al., "Influence of cholesterol on liposome stability and on in vitro drug release", Drug Delivery and Translational Research, 5(3):231-242 (2015).

Allen, et al., "Liposomal drug formulations. Rationale for development and what we can expect for the future", Drugs, 56(5):747-56 (1998).

De La Vega, et al., "Uniform polymer microspheres: monodispersity criteria, methods of formation and applications", Nanomedicine, 8(2):265-285 (2013).

Deacon, et al., "An isoform-selective, small-molecule inhibitor targets the autoregulatory mechanism of p21-activated kinase", Chem. Biol., 15(4):322-331 (2008).

Eswaran, et al., "Crystal Structures of the p21-activated kinases PAK4, PAK5, and PAK6 reveal catalytic domain plasticity of active group II PAKs", Structure, 15(1):201-213 (2007).

Gabizon, et al., "Liposomes as a drug delivery system in cancer chemotherapy", Horiz. Biochem. Biophys., 9:185-211 (1989).

Goc, et al. "Rac1 activation driven by 14-3-3ζ dimerization promotes prostate cancer cell-matrix interactions, motility and transendothelial migration", PLoS One., 7(7): e40594 (2012).

Goc, et al., "P21 activated kinase-1 (Pak1) promotes prostate tumor growth and microinvasion via inhibition of transforming growth factor β expression and enhanced matrix metalloproteinase 9 secretion", J. Biol. Chem., 288(5):3025-35 (2013).

Haeri, et al., "Preparation and Characterization of Stable Nanoliposomal Formulation of Fluoextine as a Potential Adjuvant Therapy for Drug-Resistant Tumors", Iranian Journal of Pharmaceutical Research, 13(Suppl):1-14 (2013).

Cheetham, "Novel protein kinases and molecular mechanisms of autoinhibition", Curr. Opin. Struct. Biol., 14(6):700-705 (2004).

Ke, et al., "PAK1 is a novel cardiac protective signaling molecule", Front Med., 8(4): 399-403 (2014).

Koth, et al., "Participation of group I p21-activated kinases in neuroplasticity", J. Physiol. Paris., 108(4-6): 270-7 (2014).

Lasic, et al., "Sterically stabilized liposomes: a hypothesis on the molecular origin of the extended circulation times", Biochimica. et biophysica. acta., 1070(1):187-92 (1991).

Marra, et al., "New self-assembly nanoparticles and stealth liposomes for the delivery of zoledronic acid: a comparative study", Biotechnology advances., 30(1):302-309 (2012).

Muggia, et al., "Liposomal encapsulated anthracyclines: new therapeutic horizons", Current Oncol., 3(2):156-162 (2001).

Paphajopoulos, et al., "Sterically stabilized liposomes: improvements in pharmacokinetics and antitumor therapeutic efficacy", PNAS, 88:11460-11464 (1991).

Immordino, et al., "Stealth liposomes: review of the basic science, rationale, and clinical applications, existing and potential", International Journal of Nanomedicine, 1(3):297-315 (2006).

Kumar, et al., "p21-activated kinases in cancer", Nat. Rev. Cancer., 6:459-471 (2006).

Mock, et al., "Evidence for distinct mechanisms of uptake and antitumor activity of secretory phospholipase A2 responsive liposome in prostate cancer", Integr. Biol. (Camb), 5:172-82 (2013).

Parrini, et al., "Spatiotemporal regulation of the Pak1 kinase", Biochemical Society Transactions., 33:646-8 (2005).

Kichina, et al., "PAK1 as a therapeutic target", Expert Opin. Ther. Targets., 14: 703-25 (2010).

Maeda, et al., "Tumor vascular permeability and the EPR effect in macromolecular therapeutics: a review", J Control. Release., 65:271-84 (2000).

Porchia, et al., "A Celecoxib Derivative, Directly Targets p21 Activated Kinase." Mol Pharmacol. 2007.

Nheu, et al., "The K252a derivatives, inhibitors for the PAK/MLK kinase family selectively block the growth of RAS transformants.", Cancer J. 8(4):328-336 (2002).

Radu, et al., "PAK signalling during the development and progression of cancer", Nature Reviews Cancer., 14:13-25 (2014).

Schrantz, et al., "Mechanism of p21-activated kinase 6-mediated inhibition of androgen receptor signaling", The Journal of biological chemistry., 279:1922-1931 (2004).

Somanath, et al., "14-3-3beta-Rac1-p21 activated kinase signaling regulates Akt1-mediated cytoskeletal organization, lamellipodia formation and fibronectin matrix assembly", Journal of cellular physiology., 218:394-404 (2009).

Torchilin, et al., "Multifunctional nanocarriers", Advanced Drug Delivery Reviews, 58(14):1532-55 (2006).

Taglieri, et al., "P21-activated kinase in inflammatory and cardiovascular disease", Cellular Signalling., 26:2060-2069 (2014).

Sharma, et al., "Liposome-mediated therapy of intracranial brain tumors in a rat model", Pharm Res., 14 (8):992-998 (1997).

Rudolph, et al., "Inhibitors of p21-activated kinases (PAKs).", J Med Chem. 58: 111-129 (2015).

Quach, et al., "Role of the phospholipase A2 receptor in liposome drug delivery in prostate cancer cells", Mol. Pharm., 11(10):3443-51 (2014).

Wang, et al., "Novel insights into mechanisms for Pak1-mediated regulation of cardiac Ca(2+) homeostasis", Frontiers in Physiology., 6:76 (2015).

Zhu, et al., "Secretory phospholipase A2 responsive liposomes", J Pharm Sci., 100(8):3146-3159 (2011).

Yuan, et al., "Microvascular permeability and interstitial penetration of sterically stabilized (stealth) liposomes in a human tumor xenograft", Cancer Research, 54(13):3352-3356 (1994).

(56) References Cited

OTHER PUBLICATIONS

Extended European Search Report in European Application No. 17753707.3, European regional phase entry of PCT/US2017/017828, four pages, dated Sep. 26, 2019.
Yi, et al., "Development of small-molecule inhibitors of the group 1 p21-activated kinases, emerging therapeutic targets in cancer", Biochemical Pharmacology, 80(5):683-689 (2010).
International Search Report for PCT/US2017/017828, dated Apr. 28, 2017.

* cited by examiner

IPA-3-LOADED LIPOSOMES AND METHODS OF USE THEREOF

CROSS REFERENCE TO RELATED APPLICATIONS

This application is a continuation of U.S. application Ser. No. 16/077,980, filed Aug. 14, 2018, which is a National Phase application under 35 U.S.C. 371 of PCT/US2017/017828, filed Feb. 14, 2017, which claims the benefit of and priority to U.S. Provisional Application No. 62/295,331, filed Feb. 15, 2016, which are hereby incorporated herein by reference in their entireties.

STATEMENT REGARDING FEDERALLY SPONSORED RESEARCH

This invention was made with government support under grant number W81XH -16-1-0611 and W81XH-16-1-0612 awarded by the U.S. Army Medical Research (DODAMR). The government has certain rights in the invention. (37 CFR § 401.14 f (4)).

FIELD OF THE INVENTION

The field of the invention is generally related to lipid-based delivery vehicles, particularly IPA-3-loaded liposomes and methods of use thereof, particularly in the treatment of prostate cancer.

BACKGROUND OF THE INVENTION

P21 activated kinases (PAKs), which exist in 6 different isoforms, are categorized into group-I and group-II PAKs based on their distinctly different mechanisms of activation and their non-redundant role in the regulation of cellular function (Kichina, et al., *Expert Opin Ther Targets.* 2010; 14: 703-25). Group-I PAKs, PAK-1 and PAK-2 in particular, have been implicated in various cancers (Radu, et al., *Nature reviews Cancer.* 2014; 14: 13-25). Although PAK-1 is the most expressed PAK isoform in the majority of tissues, the expression level of PAK-1 is below the detectable range in normal prostate tissue and prostatic epithelial cells (Kichina, et al., *Expert Opin Ther Targets.* 2010; 14: 703-25). Instead, normal prostate abundantly expresses group-II PAKs such as PAK-4 and PAK-6 (Schrantz, et al., *The Journal of biological chemistry.* 2004; 279: 1922-31). A previous study demonstrated that Rac1-mediated cytoskeletal remodeling is essential for prostate cancer invasion (Goc, et al. *PLoS One.* 2012; 7: e40594). Group-I PAKs are the major downstream effectors of Rac1 in mediating cytoskeletal remodeling (Somanath, et al., *Journal of cellular physiology.* 2009; 218: 394-404; Parrini, et al., *Biochemical Society transactions.* 2005; 33: 646-8.), and further investigation of the role of PAK-1 in prostate cancer revealed that although not detected in the human prostatic epithelial cells, normal prostate gland and benign prostatic hyperplasia tissues, PAK-1 is abundantly expressed in prostate tumor biopsies and metastasized colonies harbored in the human lung tissues (Goc, et al., *J Biol Chem.* 2013; 288: 3025-35). PAK-1 has also been shown to be important for the growth of prostate PC-3 cell tumor xenografts in athymic nude mice as well as transforming growth factor-β (TGFβ)-induced prostate cancer cell epithelial-to-mesenchymal transition (Al-Azayzih, et al., *Biochim Biophys Acta.* 2015; 1853: 1229-39).

Among the known inhibitors of PAKs, a reliable inhibitor and one specific to group-I PAKs is the 'inhibitor targeting PAK-1 activation-3' (IPA-3), a compound identified through high throughput screening (Deacon, et al., *Chem Biol.,* 2008; 15: 322-31). A major advantage of IPA-3 is that, unlike other kinase inhibitors, IPA-3 does not interact with and compete for the ATP-binding domain of the kinase (Rudolph, et al., *J Med Chem.* 2015; 58: 111-29). Instead, it is a non-competitive, allosteric inhibitor of PAK-1 that inhibits PAK-1 activation, even at higher ATP levels. However, the chemically and metabolically labile nature of IPA-3 becomes a major bottleneck in its use for therapeutic purpose (Rudolph, et al., *J Med Chem.* 2015; 58: 111-29). Although IPA-3 inhibits prostate cancer cellular function in vitro and tumor growth in vivo, increased frequency (i.e., daily) of drug administration was necessary (Goc, et al., *J Biol Chem.* 2013; 288: 3025-35, Al-Azayzih, et al., *Biochim Biophys Acta.* 2015; 1853: 1229-39). Further, since PAK-1 is necessary for many physiological events (Ke, et al., *Front Med.* 2014; 8: 399-403-14; Koth, et al., *J Physiol Paris.* 2014; 108: 270-7; Taglieri, et al., *Cellular signalling.* 2014; 26: 2060-9; Wang, et al., *Frontiers in physiology.* 2015; 6: 76). Serious toxic side effects of targeting PAK-1 with the free form of IPA-3 cannot be ruled out.

Thus there is a need for improved compositions and methods of delivering IPA-3 to cancer cells, particularly prostate cancer cell, in vivo.

It is an object of the invention to provide compositions and methods of use thereof that improve the in vivo stability, efficacy, or combination thereof of IPA-3.

It is a further object of the invention to provide compositions and methods of administration thereof that reduce the frequency of drug administration, reduce any potential side-effects, or combinations thereof of IPA-3.

SUMMARY OF THE INVENTION

Lipid-based delivery vehicles are provided. Nanoparticulate compositions typically including a p21 activated kinase (PAK) inhibitor and a lipid-based delivery vehicle are also provided. The lipid-based delivery vehicle can be a liposome, for example a sterically-stabilized liposome. In one embodiment, the nanoparticulate composition has a polydispersity index (PDI) of about 0.05 to about 0.139, a zeta potential of about −28.1 v, or a combination thereof. The nanoparticulate composition can have a diameter of, for example, about 75 nm to about 500 nm, or about 100 nm to about 250 nm, or about 125 nm to about 150 nm.

Typically the nanoparticulate composition includes a lipid-based delivery vehicle including one or more phospholipids, and optionally a sterol. In some embodiments, at least one of the phospholipids is PEGylated. In one embodiment, the nanoparticulate composition includes DSPC, DSPE-PEG2000, and cholesterol. In an exemplary embodiment, the ratio of DSPC, DSPE-PEG, and cholesterol is 9:1:5.

The nanoparticulate composition typically includes a PAK inhibitor, preferably a PAK-1 inhibitor, though other active agents are contemplated. The compositions can increase the half-life of the active agent in vitro or in vivo. An exemplary PAK-1 inhibitor is "Inhibitor targeting P21-activated kinase-1 (PAK1) activation-3" (IPA-3) or a derivative, prodrug, or pharmaceutically acceptable salt thereof. The disclosed formulations typically include an effective amount of a p21 a PAK inhibitor and a lipid-based delivery vehicle to, for example, inhibit or reduce tumor burden in a subject in need thereof. Pharmaceutical compositions and dosage units thereof including the nanoparticulate composition and a pharmaceutically acceptable carrier are also provided. In some embodiments, the dosage unit includes an effective amount of nanoparticulate composition to treat cancer in a subject in need thereof for 2 to 5 days for example by reducing tumor size or tumor burden or inhibit the growth or progression of tumors.

Methods of delivering active agents in vitro and in vivo using the disclosed compositions are also provided. For example, methods of treating cancer can include administering a subject in need thereof the pharmaceutical composition including a nanoparticulate composition including an active agent, most typically a PAK inhibitor, in an effective amount to treat cancer. In one embodiment, the cancer cells express PAK-1 at a higher expression level than non-cancerous cells of the same cell type. Exemplary cancers that can be treated include, but are not limited to, prostate cancer and breast cancer.

Methods of reducing PAK activity in a subject in need thereof including administering to the subject an effective amount of the pharmaceutical composition formulated to increase the half-life of the PAK-1 inhibitor in the subject to reduce PAK expression or activity are also provided. In some embodiments, the subject has prostate cancer or breast cancer.

Dosage regimens are also provided. Typically a nanoparticulate composition including an active agent such as a PAK inhibitor can be administered less frequently and achieve the same effect as administration of free-drug. Additionally, or alternatively, less active agent such as a PAK inhibitor can be administered to the subject by formulating the PAK inhibitor into a nanoparticulate composition. In some embodiments, the nanoparticulate composition is administered to a subject between about 1 and 3 times per week. In specific embodiments, the composition is administered 2 times per week.

DETAILED DESCRIPTION OF THE INVENTION

I. Definitions

Figure 1A:
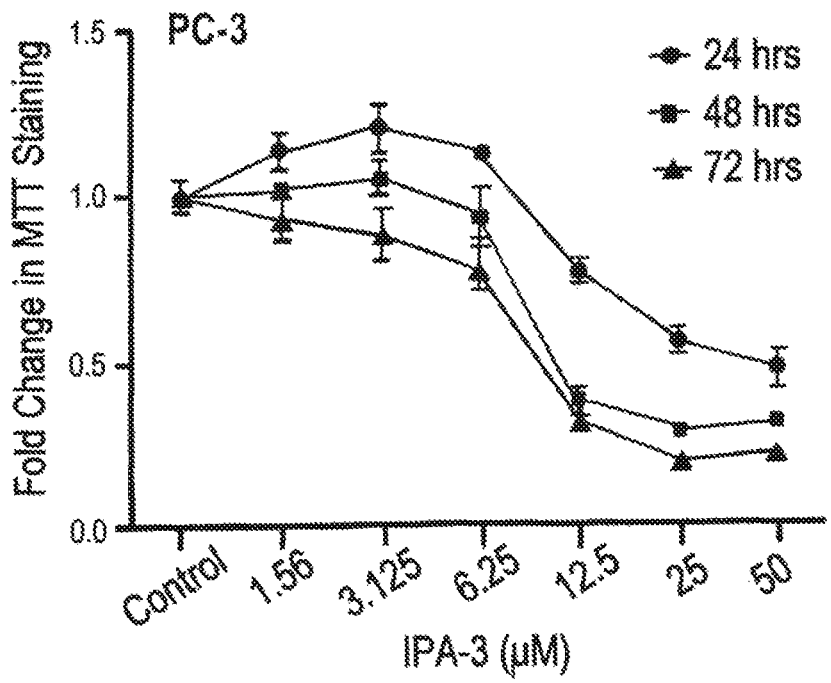
FIGS. 1A-1C are line graphs showing dose-and time-dependent effect of free IPA-3 on MTT staining in human prostate cancer PC-3 (1A), LNCaP (1B) and DU-145 (1C) cells, 24, 48, and 72 hrs after treatment (n=3).

"Active agent" as used herein refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder. An exemplary active agent is a PAK-1 inhibitor.

"Hydrophobic" as used herein refers to a non-polar molecule or part of a molecule that cannot form energetically favorable interactions with water molecules and therefore does not dissolve in water.

"Hydrophilic" as used herein describes a polar molecule or part of a molecule that forms enough energetically favorable interactions with water molecules to dissolve readily in water.

"Amphiphilic" as used herein describes a molecule having both hydrophobic and hydrophilic regions, as in a phospholipid or a detergent molecule.

"Effective amount" or "suitable amount" as used herein is at least the minimum concentration required to effect a measurable improvement or prevention of any symptom or a particular condition or disorder, to effect a measurable enhancement of life expectancy, or to generally improve patient quality of life. The effective amount is thus dependent upon the specific biologically active molecule and the specific condition or disorder to be treated. With regard to cancer, an effective amount refers to an amount of the active agent that reduces or inhibits tumor growth or tumor burden.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Sterically-stabilized liposomes" as used herein are liposomes with a modification (e.g., PEGylation) that increases the half-life of the liposome in vivo relative to the corresponding unmodified liposome.

"SSL-IPA-3" as used herein refers to a sterically-stabilized liposome loaded with 'inhibitor targeting PAK-1 activation-3' (IPA-3).

II. Compositions

Lipid-based delivery vehicles are provided. Lipid-based nanoparticulate compositions including an active agent, most typically a PAK inhibitor such as IPA-3 encapsulated, loaded into, attached to the surface of, and/or enclosed within a lipid-based delivery vehicle, and pharmaceutical compositions thereof are also provided.

A. Lipid-Based Nanoparticulate Compositions

The disclosed lipid-based nanoparticulate compositions typically include an effective amount of a PAK inhibitor such as IPA-3. The compositions can be formulated as liposomes. The term "liposome" refers to a spherical vesicle composed of at least one bilayer of amphipathic molecules which forms a membrane separating an intravesicular medium from an external medium. The intravesicular medium constitutes the internal aqueous core of the liposome. Hydrophilic molecules or components, can be encapsulated inside the internal aqueous core of the liposome via active methods of encapsulation known in the art and described below. Hydrophobic molecules or components can be entrapped inside the membrane.

An exemplary nanoparticulate delivery vehicle is a liposome. The liposomes can be, for example, multilamellar vesicles (MLV), small unilamellar liposome vesicles (SUV), large unilamellar vesicles (LUV), or cochleate vesicles. In some embodiments, the delivery composition is a micelle, or another lipid-based delivery vehicle. See, for example, Torchilin, et al., *Advanced Drug Delivery Reviews*, 58(14): 1532-55 (2006), which is specifically incorporated by reference herein in its entirety.

1. Lipids

Liposomes and other lipid-based delivery vehicles useful for the disclosed compositions are formed from one or more lipids, which can be neutral, anionic, or cationic at physiologic pH. In some embodiments, the liposomes are formed of one or more of 1,2-distearoyl-sn-glycero-3-phosphatidylcholine (DSPC), 1,2-distearoyl-snglycero-3-phosphatidylethanolamine (DSPE), and 1,2-distearoyl-sn-glycero-3-phosphoethanolamine-N-[poly (ethyleneglycol) 2000 (DSPE-PEG) and can include a sterol. In particular embodiments, such as those in the Examples below, the liposomes are sterically stabilized liposomes including DSPC, DSPE-PEG, and cholesterol.

Other lipids and components useful in preparing the disclosed nanoparticulate compositions are known in the art. Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including, but limited to, 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids. Liposomes can be generated from a single type of lipid, or a combination of two or more lipids.

The liposomes may include a sphingomyelin metabolite. Sphingomyelin metabolites used to formulate the liposomes include, without limitation, ceramide, sphingosine, or sphingosine 1-phosphate. The concentration of the sphingomyelin metabolites included in the lipids used to formulate the liposomes can range from about 0.1 mol % to about 10 mol %, or from about 2.0 mol % to about 5.0 mol %, or can be in a concentration of about 1.0 mol %.

Suitable cationic lipids in the liposomes include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N-(N',N'-dimethylamino-ethane)carbamoyl]cholesterol (DC-Chol); 2,3-dioleoyloxy-N-(2-(sperminecarboxamido)-ethyl)-N,N-dimethyl-l-propanaminium trifluoro-acetate (DOSPA), β-alanyl cholesterol, cetyl trimethyl ammonium bromide (CTAB), $diC_{14}$-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl)imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

The lipids can be formed from a combination of more than one lipid, for example, a charged lipid may be combined with a lipid that is non-ionic or uncharged at physiological pH. Non-ionic lipids include, but are not limited to, cholesterol and DOPE (1,2-dioleolylglyceryl phosphatidylethanolamine).

A sterol component may be included to confer the liposome suitable physicochemical and biological behavior. Such a sterol component may be selected from cholesterol or its derivative e.g., ergosterol or cholesterolhemisuccinate, but it is preferably cholesterol. Cholesterol is often used in lipidic formulation of liposomes because it is generally recognized that the presence of cholesterol decreases their permeability and protects them from the destabilizing effect of plasma or serum proteins.

2. Methods of Making

Liposomes typically have an aqueous core. The aqueous core can contain water or a mixture of water and alcohol. Suitable alcohols include, but are not limited to, methanol, ethanol, propanol, (such as isopropanol), butanol (such as n-butanol, isobutene, sec-butanol, tart-butanol, pentane (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

The liposomes have either one or several aqueous compartments delineated by either one (unilamellar) or several (multilamellar) phospholipid bilayers (Sapra, et al., *Curr. Drug Deliv.*, 2, 369-81 (2005)). Multilamellar liposomes have more lipid bilayers for hydrophobic therapeutic agents to associate with. Thus, potentially greater amounts of therapeutic agent are available within the liposome to reach the target cell.

Depending on the mode of preparation, the size and the degree of lamellarity of the vesicles can be tuned. Several methods for preparing unilamellar lipidic vesicles have been described in the literature: reverse phase evaporation (Szoka et al., *PNAS*, 1978; 75(9):4191-4198), ethanol injection (Pons et al. *International Journal of Pharmaceutics*, 1993; 95(1-3):51-56), heating method (Mozafari et al., *Journal of Biotechnology*, 2007; 129:604-613), but the most simple is the lipid film hydration method (Bangham et al., J. Mol. Bio., 1965; 13:238-252).

Briefly, in the lipid film hydration method, lipids are solubilized in an organic solvent such as chloroform. After homogenization of the solution, the organic solvent is evaporated under a nitrogen stream. The as-obtained dried lipid film is then hydrated by an aqueous medium at a temperature above the main phase transition temperature $T_m$, leading to the formation of multilamellar vesicles with sizes ranging from 100 to 800 nm (Mills J. K. et al. Methods in Enzymology 2004; 387:82-113). Cycles of dehydration and rehydration, by respectively freezing (in liquid nitrogen) and thawing the solution (at a temperature above $T_m$), allow increasing the aqueous internal volume by forming unilamellar vesicles. A process allowing vesicles size calibration can be applied to obtain a homogeneous size distribution.

Sonication produces Small Unilamellar Vesicles (SUV) with size ranging from 20 to 50 nm, whereas extrusion process through a filter membrane produces Large Unilamellar Vesicles (LUV) with size ranging from 50 to 500 nm depending on the size of the filter pores. Both processes, sonication and extrusion, are performed at a temperature above $T_m$.

3. Modifications a. Steric Stabilization

The liposome can be a "long circulating liposome." In the most preferred embodiments, the liposome is a sterically-stabilized or so-called "stealth" liposome. In addition to modulating the lipid composition, size, and charge of the vesicle to increase in vivo circulation, liposomal surfaces can be modified, for example, with glycolipids or sialic acid. A significant step in the development of long-circulating liposomes came with inclusion of the synthetic polymer poly-(ethylene glycol) (PEG) in liposome composition (see, e.g., Paphajopoulos, et al., *PNAS,* 88:11460-11464 (1991). The presence of PEG on the surface of the liposomal carrier has been shown to extend blood-circulation time while reducing mononuclear phagocyte system uptake. Further, by synthetic modification of the terminal PEG molecule, stealth liposomes can be actively targeted with monoclonal antibodies or ligands. Liposomes, including long circulating liposomes and stealth liposomes are reviewed in Immordino, et al, *Int J Nanomedicine,* 1(3):297-315 (2006)), which is specifically incorporated by reference herein in its entirety.

In a preferred embodiment the liposome includes a phospholipid-PEG conjugate. In liposomes composed of phospholipids and cholesterol, the ability of PEG to increase the circulation lifetime of the vehicles has been found to depend on both the amount of grafted PEG and the length or molecular weight of the polymer (Allen, et al., *Biochim Biophys Acta.,* 1066:29-36 (1991)). In most cases, the longer-chain PEGs have produced the greatest improvements in blood residence time. For example, Allen et al reported that blood levels were higher for SM/PC/CHOL/DSPE-PEG liposomes with longer molecular weight PEG (i.e., PEG 1900 and PEG 5000) than for liposomes containing PEG-lipid with a shorter chain PEG (i.e., PEG 750 and PEG 120). The presence of PEG 2000 doubled the amount of lipid remaining in the plasma compared to formulations containing PEG 350 to 750. In some embodiments, the PEG is about PGE 350 to about PEG 5000, or between about PEG 750 and about PEG 5000, or between about PEG 1000 and PEG 3000. In a particular embodiment, the PEG is PEG 2000.

In the most preferred embodiments, the nanoparticulate composition is a sterically-stabilized liposome. Lipid-based nanoparticulate drug carriers, such as long-circulating sterically-stabilized liposomes (SSL) have the ability to stably encapsulate drugs and facilitate drug delivery (Muggia, et al., *Current Oncol.* 2001; 3: 156-62; Zhu, et al., *J Pharm Sci.* 2011; 100: 3146-59; Marra, et al., *Biotechnology advances.* 2012; 30: 302-9.). They can alter the pharmacokinetics of the drug, especially compared to free drug and sometimes enhance their pharmacological activity (Muggia, et al., *Current Oncol.* 2001; 3: 156-62). Tumor specific drug delivery using lipid-based nanoparticulate drug carriers, such as SSL, have been used to encapsulate and release drugs, often with higher efficiency compared to free drug (Gabizon, et al., *Horiz Biochem Biophys.* 1989; 9: 185-211). Differences in the half-life and/or tissue and tumor distribution are believed to be primary drivers for these actions. Additionally, SSL are also believed to decrease off-targeted toxicity (Lasic, et al.,

*Biochimica et biophysica acta.* 1991; 1070: 187-92, Sharma, et al., *Pharm Res.* 1997; 14: 992-8). DOXIL® is an example of a clinically approved nanoparticle-encapsulating the anti-cancer drug doxorubicin. In addition to their ability to stabilize drugs and enhance their bio-distribution, SSL accumulate passively in solid tumors due to the enhanced permeability and retention effect mediated by defects in the vasculature and lack of functional lymphatics (Maeda, et al., *J Control Release.* 2000; 65: 271-84, Yuan, et al., Cancer research. 1994; 54: 3352-6).

b. Coatings

In some embodiments, the liposome includes a biocompatible coating allows or favors the liposomes stability in a biocompatible suspension, such as a physiological fluid (blood, plasma, serum, etc.), any isotonic media or physiologic medium, for example media comprising glucose (5%) and/or NaCl (0.9%), which is typically used for a pharmaceutical administration. Such a biocompatible coating can be obtained by treating the liposome with a surface treating agent. Stability may be confirmed by dynamic light scattering of the liposomes in biocompatible suspension. The coating can preserve the integrity of the liposome in vivo, ensure or improve its biocompatibility, facilitate its optional functionalization (for example with spacer molecules, biocompatible polymers, targeting agents, proteins, etc.), or a combination thereof.

The coating can be non-biodegradable or biodegradable. Examples of non-biodegradable coatings are one or more materials or surface treating agents selected in the group consisting of sugar (agarose for example), saturated carbon polymers (polyethylene oxide for example), reticulated or not, modified or not (polymethacrylate or polystyrene for example), as well as combinations thereof. Examples of biodegradable coatings are for example one or more materials or surface treating agents selected from the group consisting of a biological molecule, modified or not, natural or not and a biological polymer; modified or not, of natural shape or not. The biological polymer may be a saccharide, an oligosaccharide or a polysaccharide, polysulfated or not, for example dextran.

c. Targeting

The surface of the liposomes or components thereof can be modified to facilitate targeting through the attachment of targeting molecules. Exemplary target molecules include proteins, peptides, nucleic acids, lipids, saccharides, or polysaccharides that bind to one or more targets associated with an organ, tissue, cell, or extracellular matrix, or specific type of tumor or infected cell. The degree of specificity with which the lipsomes are targeted can be modulated through the selection of a targeting molecule with the appropriate affinity and specificity. For example, a targeting moiety can be a polypeptide, such as an antibody that specifically recognizes a tumor marker that is present exclusively or in higher amounts on a malignant cell (e.g., a tumor antigen). Suitable targeting molecules that can be used to direct liposomes to cells and tissues of interest, for example cancerous tissue, as well as methods of conjugating target molecules to liposomes, are known in the art. Targeting molecules can also include neuropilins and endothelial targeting molecules, integrins, selectins, and adhesion molecules. Targeting molecules can be covalently bound to liposomes using a variety of methods known in the art.

In certain embodiments, the liposome includes one or more PEGylated lipids. The targeting molecules may be conjugated to the terminus of one or more PEG chains present on the surface of the liposomal shell.

The aforementioned materials, compounds or surface treating agents can be used alone or in combinations, mixtures or assemblies, composite or not, covalent or not, optionally in combination with other compounds.

4. Exemplary Embodiments

In preferred embodiments, the nanoparticulate composition includes a sterically-stabilized liposome including cholesterol, and phospholipids such as DSPC and DSPE-PEG. For example, lipid-based delivery vehicles such is liposomes can include DSPC, DSPE-PEG, and cholesterol in a ratio of 9:1:5. In some embodiments, the PEG is PEG2000. A preferred embodiment is exemplified in the working Examples below. Liposomes were prepared using the thin lipid hydration method followed by freeze—thaw cycles and a high-pressure extrusion (Mock, et al., Integr Biol (Camb). 2013; 5: 172-82, and Zhu, et al., *J Pharm Sci.* 2011; 100: 3146-59, each of which is specifically incorporated by reference in its entity). Liposome composition is shown in Table 1, below. Briefly, cholesterol, phospholipids including DSPC and DSPE-PEG in chloroform and drug in ethanol can be added together and the solvents evaporated under vacuum. The formed thin film can be hydrated and suspended in ammonium phosphate buffer or phosphate saline buffer (PBS) to achieve a final lipid concentration of about 10 μmol/ml. The formulation can be subjected to liquid nitrogen freeze-thaw cycles above the phase transition temperature of the primary lipid, and passed through a Lipex extruder using double stacked polycarbonate membranes. Excess un-encapsulated drug and lipids can be eliminated using dialysis.

B. Active Agents

1. PAK Inhibitor

The nanoparticulate compositions disclosed herein can include an active agent encapsulated, loaded into, attached to the surface of, and/or enclosed therein. A preferred active agent is a PAK inhibitor.

A representative PAK inhibitor has the structure:

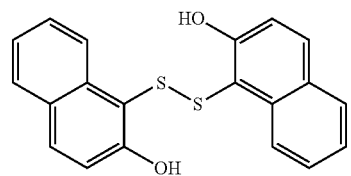 [SMILES: Oc1ccc2ccccc2c1SSc1c(O)ccc2ccccc12]

or a derivative, prodrug, or pharmaceutically acceptable salt thereof. This PAK inhibitor is named IPA-3 (1,1'-Dithiodi-2-naphthtol) and is described by Deacon et al. 2008 *Chem Biol.* 15(4):322-3, which is specifically incorporated by reference herein in its entirety. The term "derivative" or "derivatised" as used herein includes one or more chemical modifications of IPA-3, an enantiomer, polymorph, or pharmaceutically acceptable salt thereof. That is, a "derivative" may be a functional equivalent of IPA-3, which is capable of inducing the improved pharmacological functional activity and/or behavioral response in a given subject. Illustrative of such chemical modifications would be replacement of hydrogen by a halo group, an alkyl group, an acyl group or an amino group. In some embodiments, inactive or low activity derivatives and relatives such as PIR3.5 are excluded as active agents.

The chemical modification of IPA-3, an enantiomer, polymorph, or pharmaceutically acceptable salt thereof may either enhance or reduce hydrogen bonding interaction, charge interaction, hydrophobic interaction, Van Der Waals interaction or dipole interaction between the compound and its target.

In some embodiments, IPA-3 may act as a model (for example, a template) for the development of other derivative compounds which are a functional equivalent of the compound and which is capable of inducing the improved pharmacological functional activity and/or effect and/or behavioral response in a given subject.

IPA-3 may be racemic compounds and/or optically active isomers thereof. In this regard, some of the compounds can have asymmetric carbon atoms, and therefore, can exist either as racemic mixtures or as individual optical isomers (enantiomers). Compounds described herein that contain a chiral center include all possible stereoisomers of the compound, including compositions including the racemic mixture of the two enantiomers, as well as compositions including each enantiomer individually, substantially free of the other enantiomer. Thus, for example, contemplated herein is a composition including the S enantiomer of a compound substantially free of the R enantiomer, or the R enantiomer substantially free of the S enantiomer. If the named compound includes more than one chiral center, the scope of the present disclosure also includes compositions including mixtures of varying proportions between the diastereomers, as well as compositions including one or more diastereomers substantially free of one or more of the other diastereomers. By "substantially free" it is meant that the composition includes less than 25%, 15%, 10%, 8%, 5%, 3%, or less than 1% of the minor enantiomer or diastereomer(s).

IPA-3 is discussed in U.S. Pat. No. 8,771,682, and U.S. Published Application Nos. 2015/359815 and 2008/097062.

Other PAK-inhibitors are known in the art and can also be utilized. See, for example, U.S. Pat. No. 8,771,682, (Eswaran, et al., *Structure*. 2007; 15:201-213; Nheu et al., *Cancer J* 2002; 8:328-336; Porchia, et al., "A Celecoxib Derivative, Directly Targets p21 Activated Kinase."*Mol Pharmacol.* 2007) each of which is specifically incorporated by reference herein in its entirety.

2. Other Active Agents

In some embodiments, one or more additional or alternative active agents are loaded encapsulated, loaded into, attached to the surface of, and/or enclosed in the nanoparticulate composition. Thus in some embodiments, the nanoparticulate composition does not include IPA-3 or another PAK inhibitor. Other active agents include, for example, therapeutic, nutritional, diagnostic, and prophylactic agents. The active agents can be small molecule active agents or biomacromolecules, such as proteins, polypeptides, or nucleic acids. Suitable small molecule active agents include organic and organometallic compounds. The small molecule active agents can be a hydrophilic, hydrophobic, or amphiphilic compound.

Exemplary therapeutic agents that can be incorporated into the compositions include tumor antigens, CD4+T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immuno- modulators (including ligands that bind to Toll-Like Receptors (including but not limited to CpG oligonucleotides) to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of nanolipogels into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Exemplary diagnostic agents include paramagnetic molecules, fluorescent compounds, magnetic molecules, and radionuclides, x-ray imaging agents, and contrast agents.

Representative active agents including chemotherapeutic agents are discussed in more detail below with respect to combination therapies.

In certain embodiments, the composition contains two or more active agents.

C. Pharmaceutical Compositions

Pharmaceutical compositions including liposome or other lipid-based delivery compositions are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example, by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the drug to the immediate area of the implant.

The liposome compositions can be provided to the cell either directly, such as by contacting it with the cell, or indirectly, such as through the action of any biological process. For example, the liposomes can be formulated in a physiologically acceptable carrier or vehicle, and injected into a tissue or fluid surrounding the cell.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. Generally, the total amount of the liposome-associated active agent administered to an individual will be less than the amount of the unassociated active agent that must be administered for the same desired or intended effect and/or may exhibit reduced toxicity.

1. Formulations for Parenteral Administration

In a preferred embodiment the compositions are administered in an aqueous solution, by parenteral injection.

The formulation can be in the form of a suspension or emulsion. In general, pharmaceutical compositions are provided including effective amounts of one or more active agents optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Other Formulations

The liposome compositions can be applied topically. Topical administration can include application to the lungs, nasal, oral (sublingual, buccal), vaginal, or rectal mucosa. These methods of administration can be made effective by formulating the liposome with transdermal or mucosal transport elements. For transdermal delivery such elements may include chemical enhancers or physical enhancers such as electroporation or microneedle delivery. For mucosal delivery PEGylation of the liposome or addition of chitosan or other mucosal permeants or PH protective elements for oral delivery is preferred.

Liposomes can be delivered to the lungs (Taylor and Newton, *Thorax*. 1992 April; 47(4): 257-259). A wide range of mechanical devices designed for pulmonary delivery of therapeutic products can be used, including but not limited to, nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Liposomes have also been formulated for oral delivery (Woodley, Crit Rev Ther Drug Carrier Syst. 1985; 2(1):1-18; Hua, *Front Pharmacol*. 2014; 5: 138, etc.). Oral formulations may be in the form of chewing gum, gel strips, tablets, capsules, or lozenges. Oral formulations may include excipients or other modifications to the particle which can confer enteric protection or enhanced delivery through the GI tract, including the intestinal epithelia and mucosa (see Samstein, et al., *Biomaterials*, 29(6):703-8 (2008).

Transdermal formulations may also be prepared. These will typically be ointments, lotions, sprays, or patches, all of which can be prepared using standard technology. Transdermal formulations can include penetration enhancers. Chemical enhancers and physical methods including electroporation and microneedles can work in conjunction with this method.

III. Methods of Use

The nanoparticulate compositions can be used to deliver active agents in vitro and in vivo. A typical in vivo method includes administering to a subject in need thereof an effective amount of an active agent-loaded nanoparticulate composition to reduce one or more symptoms of a disease or disorder.

In general, the disclosed compositions and methods of treatment thereof are useful in the context of cancer, including tumor therapy. Accordingly, methods of treating cancer are provided. For embodiments in which at least one of the active agents is a PAK inhibitor such as IPA-3, the cancer is typically a PAK-1 positive cancer, for example a prostate cancer or a breast cancer. The methods typically include administering a subject in need there of an effective amount to the composition to reduce one or more symptoms of cancer. For example, therapeutically effective amounts of the disclosed compositions used in the treatment of cancer will generally kill tumor cells or inhibit proliferation or metastasis of the tumor cells or a combination thereof. Symptoms of cancer may be physical, such as tumor burden, or biological such as apoptosis of cancer cells. For example, the composition can be administered in an amount effective to kill cancer cells, improve survival of a subject with cancer, or a combination thereof. The actual effective amounts of composition can vary according to factors including the specific, the particular composition formulated, the mode of administration, and the age, weight, condition of the subject being treated, as well as the route of administration and the disease or disorder.

An effective amount of the composition can be compared to a control. Suitable controls are known in the art. A typical control is a comparison of a condition or symptom of a subject prior to and after administration of the composition. The condition or symptom can be a biochemical, molecular, physiological, or pathological readout. In another embodiment, the control is a matched subject that is administered a different therapeutic agent. Accordingly, the compositions disclosed here can be compared to other art recognized treatments for the disease or condition to be treated. In a preferred embodiment, the results achieved with a composition including a nanoparticulate delivery vehicle and drug is compared to the results achieved by free drug (e.g., drug without delivery vehicle).

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

1. Subjects to be Treated

Tumors, for example malignant tumors, which may be treated are classified herein according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterine. In the most preferred embodiments, the cancer is prostate cancer or breast cancer.

In some embodiments, the disclosed compositions are used to treat multiple cancer types concurrently. The compositions can also be used to treat metastases or tumors at multiple locations.

Serine-threonine kinases PAKs, PAK-1 in particular, have been associated with a variety of pathological conditions, including cancer (Kichina, et al., *Expert Opin Ther Targets*. 2010; 14: 703-25). PAK-1 is regulated by auto-inhibition, and is believed to be a good therapeutic target for cancer therapy by using small molecules that may cause conformational changes in the protein disturbing its autoregulation (Kichina, et al., *Expert Opin Ther Targets*. 2010; 14: 703-25, Cheetham, *Curr Opin Struct Biol*. 2004; 14: 700-5). Previous studies showed that Rac1, an upstream regulator of PAK-1 promotes prostate cancer cell survival, proliferation and transendothelial-migration (Goc, et al., *PLoS One*. 2012; 7: e40594). Although absent in the normal prostate and human benign prostatic hyperplasia tissues, studies revealed that PAK-1 is expressed in prostate cancer cells, prostate tumors and metastatic colonies in the patient lungs (Goc, et al., *J Biol Chem*. 2013; 288: 3025-35), and that PAK-1 is important in the TGFβ-induced epithelial-mesenchymal transition (EMT) in prostate cancer cells (Al-Azayzih, et al., *Biochim Biophys Acta*. 2015; 1853: 1229-39).

Therefore in some embodiments, the cancer includes cancers cells with an elevated PAK, preferably PAK-1, relative to the corresponding on non-cancer cells. See also, Kumar et al., *Nat Rev Cancer*. 2006; 6:459-471, which is specifically incorporated by reference herein in its entirety. IPA-3 also has activity against other Group I PAKS including PAK-2 and PAK-3. Therefore, in some embodiments, the cancer cells have elevated PAK-2 or PAK-3. In particularly preferred embodiments, the cancer is a prostate cancer or a breast cancer with an elevated PAK, preferably elevated PAK-1. IPA-3 will preferentially kills cells expressing or having elevated PAK-1 relative to cells with low or no PAK-1 expression. Therefore, IPA-3 can target PAK-expressing cells, particularly PAK-1 expressing cells, even without a targeting moiety.

In some embodiments, the compositions are utilized to treat a non-cancerous malady in which a PAK, particularly PAK-1, is elevated.

2. Dosage Regimens

In a screening process for allosteric inhibitors targeting PAK-1 activation, IPA-3 was identified as a small molecule inhibitor of PAK-1, and was then proposed as a potential therapeutic candidate for various human pathologies including cancer (Deacon, et al., *Chem Biol*. 2008; 15: 322-31). However, IPA-3 in its free form has a very short half-life in vivo because of its rapid metabolism (Rudolph, et al., *J Med Chem*. 2015; 58: 111-29). Thus, the metabolically labile nature of IPA-3 becomes a major bottleneck in its use for therapeutic purposes. Although the free form of IPA-3 was effective in inhibiting prostate cancer growth in our studies, this required daily administration of the drug (Al-Azayzih, et al., *Biochim Biophys Acta*. 2015; 1853: 1229-39). This demanded a reliable method to specifically deliver IPA-3 to prostate cancer cells in vivo that will improve the stability and efficacy of IPA-3, reduce the frequency of drug administration and avoid any potential side-effects of free IPA-3.

Like in the case of IPA-3, most of the laboratory based research on prostate cancer does not reach the clinic due to various issues relating to the dose, frequency of drug administration, stability of particular drug in vivo and the adverse reactions. The major limitation of many anti-cancer drugs is caused by rapid metabolism and/or toxic side effects. An ideal drug dosage formulation for anti-cancer therapy has to exhibit specific delivery of an effective dose of drug to the target tissue over the required period of time.

The Examples below show that the disclosed liposomal-drug compositions can be administered less frequently but nonetheless have a greater impact on cancer free drug. Accordingly, preferred dosage regimens are provided. In some embodiments, the composition is administered less frequently than free-drug to achieve similar, the same, or greater effect, preferably with less toxicity. In some embodiments, the dosage of the composition includes the same amount or less drug that the free-drug dosage.

The frequency of administration can be, for example, one, two, three, four or more times daily, weekly, every two weeks, or monthly. In some embodiments, the composition is administered to a subject once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the frequency of administration is once, twice or three times weekly, or is once, twice or three times every two weeks, or is once, twice or three times every four weeks. In some embodiments, the composition is administered to a subject with cancer 1-3 times, preferably 2 times, a week.

3. Combination Therapies

Combination therapies are also disclosed. The disclosed compositions can include, or can be administered to a subject in need thereof alone or in combination with one or more additional therapeutic agents. The additional therapeutic agents are selected based on the condition, disorder or disease to be treated. For example, the liposomal-drug composition can be co-administered with one or more additional agents that treat cancer. In a preferred embodiment the additional therapeutic agent targets a different pathway so that the combined effect of the therapies is greater than each alone.

The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second). The additional therapeutic agents can be administered locally or systemically to the subject, or coated or incorporated onto, or into a device or graft. The additional agent(s) can be part of the same liposome, added to different liposomes or other delivery vehicles such as polymeric nanoparticles, or administered as free-drug.

Additional therapeutic agents include conventional cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors, e.g., imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarbamide, idarubicin, ifosfamide, irinotecan, leucovorin, liposomal doxorubicin, liposomal daunorubicin, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof. Representative pro-apoptotic agents include, but are not limited to, fludarabinetaurosporine, cycloheximide, actinomycin D, lactosylceramide, 15d-PGJ(2), and combinations thereof.

IV. Kits

Dosage units including the disclosed composition, for example, in a pharmaceutically acceptable carrier for shipping and storage and/or administration are also disclosed. Components of the kit may be packaged individually and can be sterile. In some embodiments, a pharmaceutically acceptable carrier containing an effective amount of the composition is shipped and stored in a sterile vial. The sterile vial may contain enough composition for one or more doses. The composition may be shipped and stored in a volume suitable for administration, or may be provided in a concentration that is diluted prior to administration. In another embodiment, a pharmaceutically acceptable carrier containing drug can be shipped and stored in a syringe.

Kits containing syringes of various capacities or vessels with deformable sides (e.g., plastic vessels or plastic-sided vessels) that can be squeezed to force a liquid composition out of an orifice are provided. The size and design of the syringe will depend on the route of administration. Any of the kits can include instructions for use.

EXAMPLES

Example 1

Formulation and Characterization of SSL-IPA-3

Materials and Methods
Chemicals and Reagents

IPA-3 was purchased from Tocris Bioscience (Bristol, United Kingdom). The phospholipids, 1,2-distearoyl-sn-glycero phosphatidylcholine (DSPC), 1,2-distearoyl-snglycero -3-phosphatidylethanolamine (DSPE), and 1,2-distearoyl-sn-glycero -3-phosphoethanolamine—N4poly (ethyleneglycol) 2000 (DSPE-PEG) were purchased from Avanti Polar Lipids, Inc (Alabaster, Alabama). Cholesterol and MTT [3-(4,5-dimethylthiazol-2yl)-2,5diphenyltetrazolium bromide] were purchased from Sigma—Aldrich (St. Louis, Missouri). F-12K, EMEM and RPMI cell culture media and their supplements, including antibiotics and fetal bovine serum (FBS), were purchased from ATCC. All other chemicals and solvents were of analytical grade and were obtained from Fisher Scientific (Pittsburgh, PA).

Preparation of Sterically-Stabilized IPA-3 Liposomes (SSL-IPA-3)

Liposomes were prepared using the thin lipid hydration method followed by freeze—thaw cycles and a high-pressure extrusion as described previously Mock, et al., *Integr Biol (Camb)*. 2013; 5: 172-82; and Zhu, et al., *J Pharm Sci.* 2011; 100: 3146-59, each of which is incorporated by references in its entity). Liposome composition is shown in Table 1. Cholesterol (5 µmol/ml), phospholipids including DSPC (9 µmol/ml) and DSPE-PEG (1 µmol/ml) in chloroform and IPA-3 (4 µmol/ml) in ethanol were added into a round bottom flask, the solvents were then evaporated under vacuum in a water bath at 65° C. using a rotary evaporator (Buchi Labortechnik AG, Postlfach, Switzerland). The formed thin film was then hydrated and suspended in ammonium phosphate buffer (250 mM, pH 7.4) or phosphate saline buffer (PBS) to achieve a final lipid concentration of 10 µmol/ml. The formulation then underwent five liquid nitrogen freeze—thaw cycles above the phase transition temperature of the primary lipid, prior to passing five times through a Lipex extruder (Northern Lipids, Inc, Burnaby, BC Canada) at 65° C. using double stacked polycarbonate membranes (80 nm, GE Osmonics, Trevose, Pennsylvania). Excess un-encapsulated IPA-3 and lipids were eliminated using dialysis in 10% (w/v) sucrose for at least 20 hours (hrs) with three changings of the dialysis media. The liposome diameter was determined using a dynamic light scattering particle size analyzer (Zetasizer Nano ZS, Malvern Instruments, Enigma Business Park, Grovewood Road, Malvern, Worcestershire, UK).

Liposomal size was further confirmed using Tandem Electron Microscopy (TEM) imaging. Liposome suspensions were stored at 4° C., protected from light, and used within 24 to 48 hrs of preparation. Empty SSL (made without IPA-3 encapsulation) were also formulated and used as vehicle controls. 10 µl of liposomal suspension were placed on a carbon-over-Pioloform-coated copper grid and let dry out overnight. Samples were imaged the next day using TEM.

Quantification of IPA-3 in Liposomes

SSL suspensions were collected after an overnight dialysis and IPA-3 was quantified using a spectroscopic method based on its absorbance at 360 nm. Serial dilutions of IPA-3 stock solution were made in acidic ethanol. Absorbance at 360 nm was recorded using a Spectra Max M2 microplate reader (MTX Lab Systems, Inc. Vienna, Virginia 22182 U.S.A.) and plotted against the concentration of IPA-3. A standard curve ($R^2>0.99$) was used to determine the concentration of IPA-3 in SSL.

Characterization of Size, Zeta Potential and Physical Stability of Liposomal IPA-3

Figure 1B:
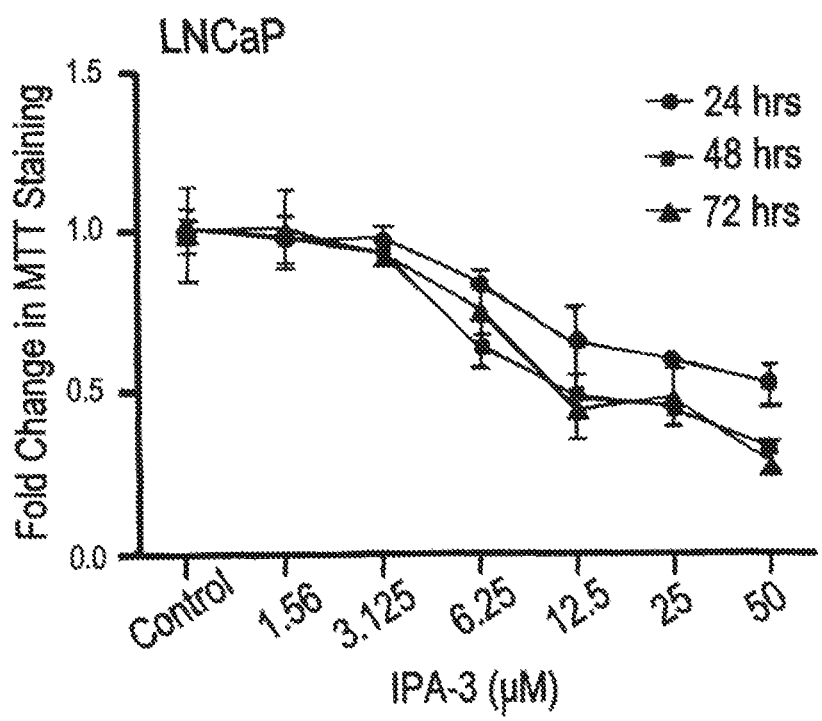
Figure 1C:
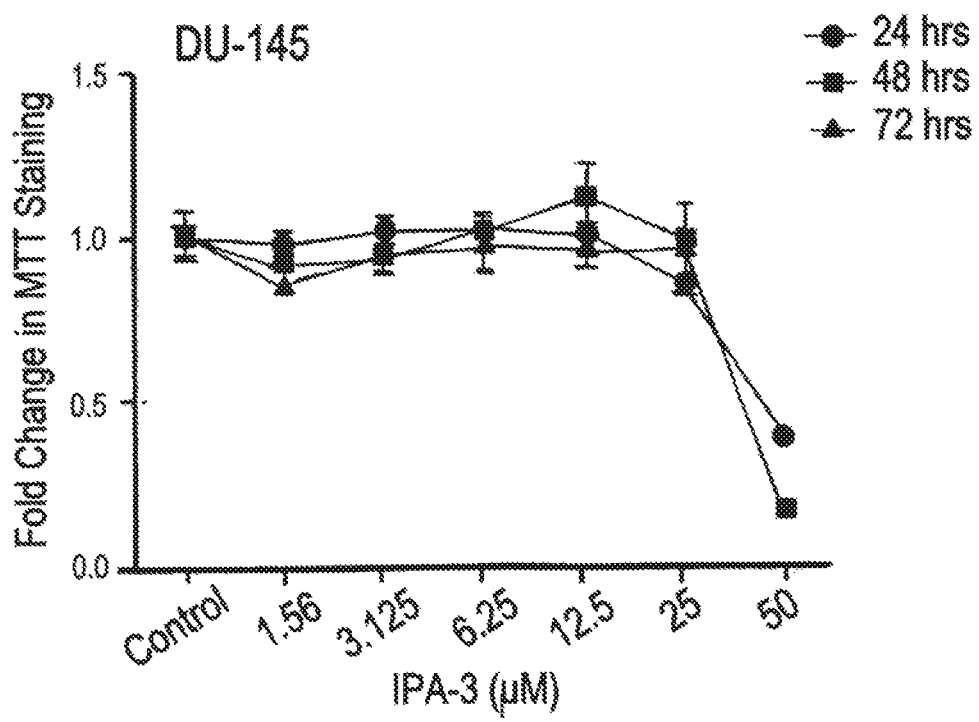
Figure 1D:
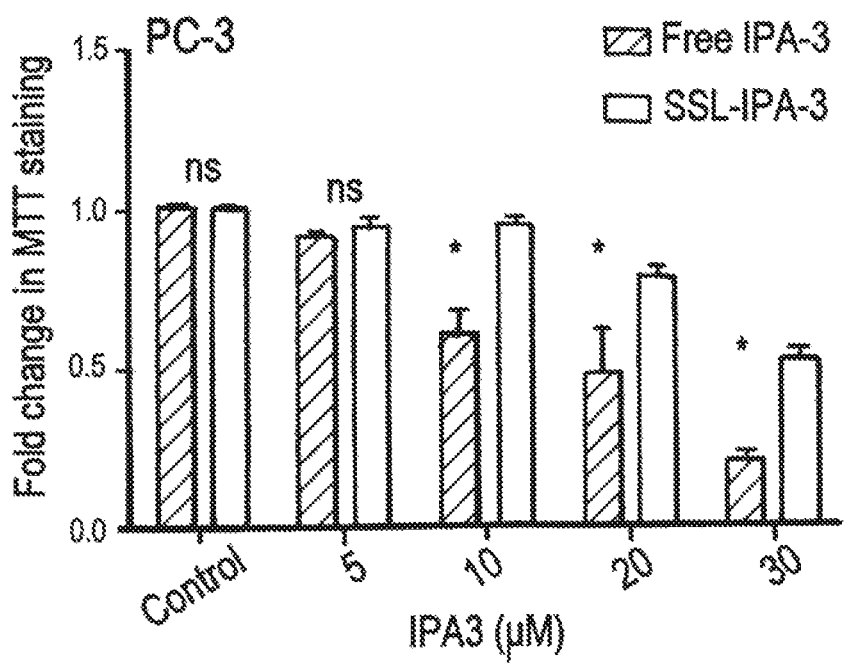
FIGS. 1D and 1E are bar graphs showing the effect of free IPA-3 and SSL-IPA-3 on MTT staining in human prostate cancer PC-3 (1D) and DU-145 (1E) cells 72 hrs after treatment (n=3). The open bars in FIG. 1D and E for control indicate the effect of empty liposomes. Data are presented as the mean±SEM of the fold change in MTT staining as function of IPA-3 concentration; *p<0.05; "NS" indicates not significant.
Figure 1E:
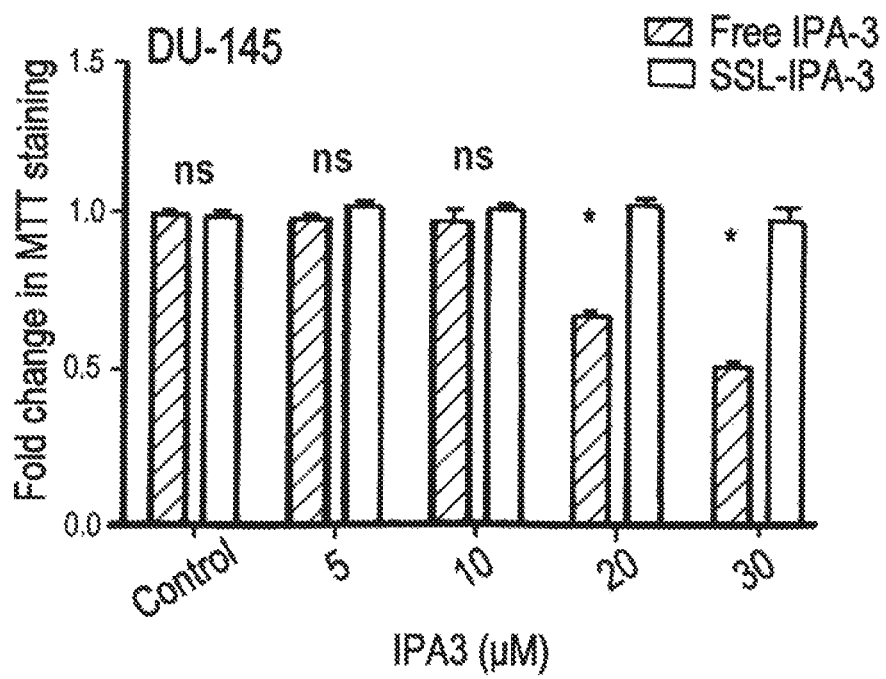
Figure 1F:
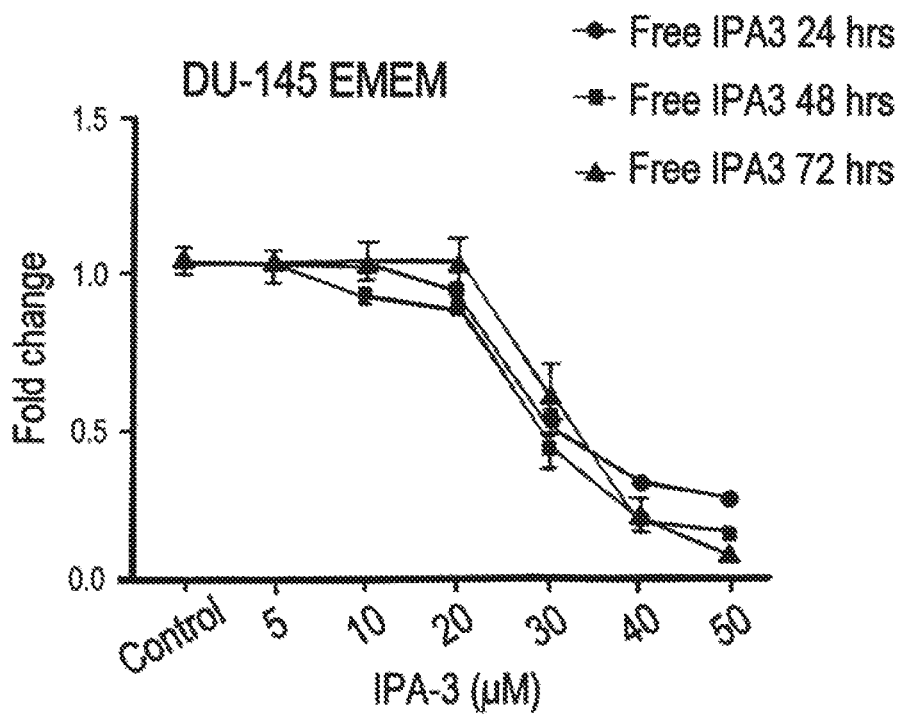
FIGS. 1F-1H are lines graphs effect of free IPA-3 on MTT staining in human prostate cancer cells (DU-145) in three different media (EMEM (1F), RPMI (1G), and F-12K (1H)) after 24, 48 and 72 h treatment. Data represent fold change in MTT staining as function of IPA3 concentration. Data are presented as the mean±SEM.
Figure 1G:
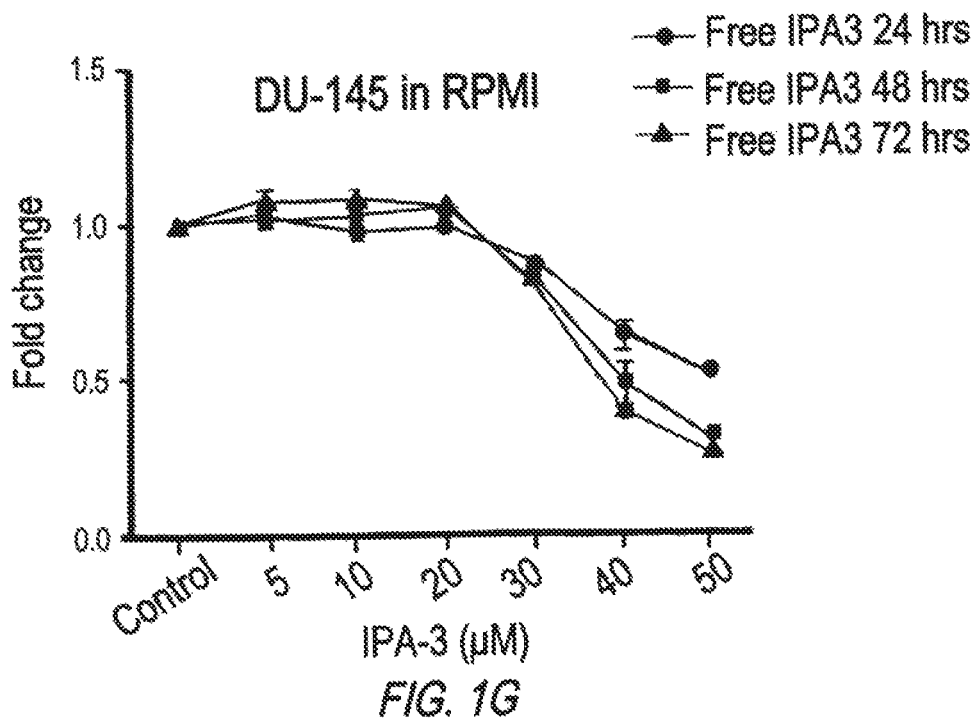
Figure 1H:
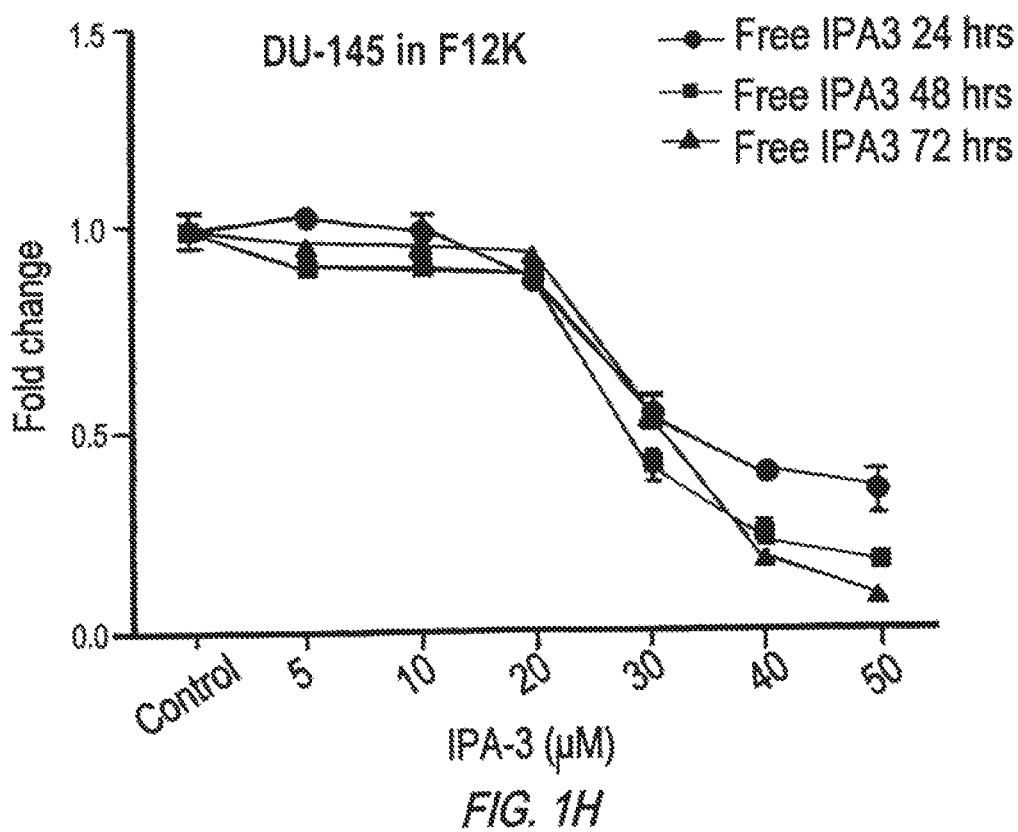
Figure 1I:
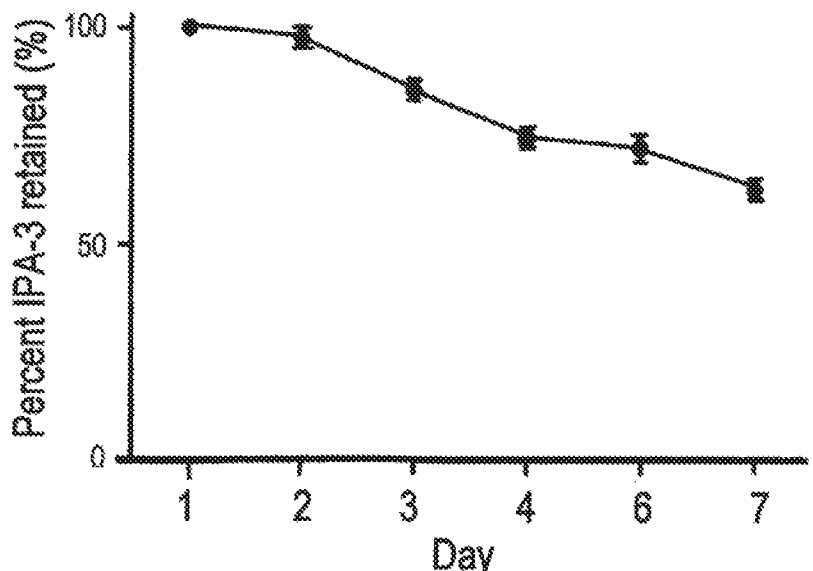
FIG. 1I is a line graphs showing percent IPA-1 retained over time (days). SSL were evaluated for their retention capacity of IPA-3 for 72 hr following reformulation. Drug leakage from liposomes was determined by removing portions of liposomes from a pool stored at pH 7.4 and 4° C. at the indicated time point. After dialysis, IPA-3 encapsulated liposomes were analyzed for IPA-3 content as described in the methods. Data are presented as the mean±SEM of the amount of IPA-3 retained as function of time.

Long circulating liposomes containing IPA-3 were evaluated for physical stability in the storage conditions at 4° C. Drug leakage from liposomes was determined by removing portions of liposome suspension from a pool stored at pH 7.4 and 4° C. at various times. IPA-3 liposomes were submitted to dialysis and reanalyzed for IPA-3 content as described above. A significant change in IPA-3 content was used as an indication of liposome stability. Changes in mean diameter and zeta potential of liposomes were also used to assess stability and was monitored overtime using a dynamic light scattering Malvern Zetasizer. Samples were diluted 1 in 10 (v/v) with PBS for the size and zeta potential measurements. As IPA-3 liposomes were to be used for in vivo studies after reconstitution, we assessed IPA-3 stability after reconstitution for increasing time periods, including 3 days, the time corresponding to in vivo dosing. The analysis showed that over 80% of IPA-3 was maintained in SSL after 3 days (FIG. 1I). In fact, good stability appeared to be maintained up to at least 7 days in reconstituted liposomes.

Results

SSL-IPA-3 (Table 1) had a hydrodynamic particle diameter of approximately 139 nm, and this value did not change significantly over a period of two weeks (Table 2). The polydispersity index (PDI), a measure of the distribution of diameters was maintained at values less than 0.14 for up to 14 days. These PDI values are within the recommended size for medical applications, which is a PDI of less than 0.3 (De La Vega, et al., Nanomedicine (London, England). 2013; 8: 265-85). The zeta potential (the overall surface charge of the particles) also did not significantly change during this time.

The stability test showed that 70% of IPA-3 was retained by these liposomes after 7 days post-formulation, and 50% was retained after 14 days. The stability tests also showed that a high amount of IPA-3 was retained in SSL after reconstitution for dosing, up to 80% after 3 days, and greater than 60% after 7 days post reconstitution (FIG. 1I). Drug leakage from liposomes was determined by removing portions of liposomes from a pool stored at pH 7.4 and 4° C. at the indicated time point. After dialysis, IPA-3 encapsulated liposomes were analyzed for IPA-3 content as described in the methods. Data are presented as the mean±SEM of the amount of IPA-3 retained as function of time.

TABLE 1

Composition of the SSL-IPA-3

| Liposome Component | Concentration |
| --- | --- |
| 1,2-distearoyl-sn-glycero-3-phosphocholine (DSPC) | 9 µmol/ml |
| 1,2-distearoyl-sn-glycero-3-phosphoethanolamine-N-[maleimide(polyethylene glycol)-2000] (DSPE-PEG) | 1 µmol/ml |
| Cholesterol | 5 µmol/ml |
| IPA-3 | 4 µmol/ml |

TABLE 2

Physical characterization of SSL-IPA-3

| | Mean Diameter (nm) | Polydispersity Index (PDI) | Zeta Potential (mV) |
| --- | --- | --- | --- |
| Day 1 | 139.3 ± 0.115 | 0.050 ± 0.090 | −28.1 ± 0.00 |
| Day 7 | 139.4 ± 2.307 | 0.121 ± 0.021 | −27.1 ± 0.451 |
| Day 14 | 137.4 ± 5.726 | 0.139 ± 0.003 | −32.8 ± 0.929 |

Example 2

SSL-IPA-3 has Anti-Tumor Activity in Various Human Prostate Cancer Cell Lines

Materials and Methods

Cell Lines and Cell Culture

The human prostate cancer cell lines PC-3, LNCaP and DU-145 and the breast cancer cell lines MCF-7 and MDA-231 were purchased from ATCC (Manassas, Va.). PC-3, LNCaP, and DU-145 cells were cultured in F12K, RPMI, and EMEM, respectively. MCF-7 and MDA-231 cells were cultured in RPMI. All culture media were supplemented with 10% FBS and 1% penicillin/streptomycin antibiotics (ATCC). All the cells were maintained at 37° C. in incubators with 5% CO2 and humidified atmosphere.

In Vitro Cytotoxicity of Liposomal IPA-3 Measured Using MTT Staining

The cytotoxicity of the liposomal IPA-3 as well as the free IPA-3 was determined in three prostate cancer cell lines (PC-3, LNCaP, and DU-145) using the MTT assay (Twentyman, et al., Br J Cancer. 1987; 56: 279-85). Free IPA-3 and SSL-IPA-3 were used for comparison. Cells were seeded in 48-well tissue culture plates at $5 \times 10^4$ cells/ml and incubated at 37° C. in a 5% CO2 incubator for 24 hr. This time was sufficient for the cells to attach and resume their growth. Liposomes were diluted in the different culture media to their final concentrations and experiments were performed in triplicates. Cells were also treated with free IPA-3 (1.56, 3.125, 6.25, 12.5, 25 and 50 µM), DMSO (vehicle for IPA-3) and empty liposomes (vehicles for encapsulated IPA-3; indicated by white bars in the controls of FIG. 1D and 1E) as controls. The cells were incubated for 24, 48, and 72 hrs. MTT was added at each time point, at a final concentration of 0.25 mg/ml and plates were incubated at 37° C. Non-reduced MTT and media were aspirated after 2 hrs and replaced with DMSO to dissolve the MTT formazen crystals. Plates were shaken for 15 min and absorbance was read at 590 nm using a Spectra Max M2 plate reader (BMG Lab Technologies, Inc., Durham, NC). The concentration of IPA-3 resulting in 50% growth inhibition (IC50) was estimated from the concentration-effect curve.

In Vitro Cytotoxicity of Liposomal IPA-3 Measured Using Annexin V and PI Staining Annexin V and PI staining plus flow cytometry was used to assess NRK cell death as previously described with modifications (Cummings, et al., *The Journal of pharmacology and experimental therapeutics*. 2002; 302: 8-17). Briefly, cells were seeded and allowed to grow for 24 h prior to addition of free IPA-3, SSL-IPA-3, or empty liposomes. After the indicated time, medium was removed and cells were washed twice with PBS and incubated in binding buffer (10 mM HEPES, 140 mM NaCl, 5 mM KCl, 1 mM MgCl2, 1.8 mM CaCl2, pH 7.4) containing annexin VFITC (25 mg/ml) and PI (25 mg/ml) for 10 min. Cells were then washed three times with binding buffer, released from monolayers using a rubber policeman, and staining quantified using a Dako Cyan ADP 9 color flow cytometer (Beckman Coulter, Inc., Miami, FL). For each measurement 10,000 events were counted.

Immunoblot Analysis

Proteins from different cell lines were collected in RIPA buffer, which contained protease inhibitor cocktail (Santa Cruz Biotechnology, Inc., Santa Cruz, CA). Protein concentrations were determined using the BCA assay. Protein samples of 40 μg were separated on SDS-PAGE gels and transferred to nitrocellulose membranes, which were then blocked in 5% (w/v) nonfat dry milk in Tris-buffered saline-Tween 20 (TBS-T) for 2 hrs. The membranes were then incubated with a rabbit PAK-1 antibody at a dilution of 1:500 in 1% (w/v) BSA TBS-T overnight. Antibodies against GAPDH (Santa Cruz Biotechnology Inc., Santa Cruz, CA) were used at a dilution of 1:200 in 1% (w/v) BSA in TBST for 1 hr. Membranes were then incubated with the appropriate peroxidase-conjugated secondary antibody (Promega, Madison, WI) used at a dilution of 1:2500. The membrane was then washed with TBS-T three times for 10 minutes each and imaged with a Fluorchem SP digital imager (Alpha Innotech, San Leandro, CA, USA). Densitometry was performed using National Institutes of Health Image J software.

Statistical Analysis

All in vitro experiments were repeated at least three times (n=3) in triplicate. Results are shown as the average of all replicates±SEM. A two way ANOVA test followed by Bonferroni posttest was used to determine whether the differences between free IPA-3 and SSL-IPA-3 treatment groups were statistically significant. A two-tailed student's t test was used to compare the differences in PAK-1 expression between different cancer cell lines, and for the direct comparison of the tumor xenograft weights. The significance level (alpha) was set at 0.05 (marked with symbols wherever data are statistically significant).

Results

The anti-tumor activity of free IPA-3 was initially determined in vitro to verify that this compound inhibited prostate cancer cell growth. Our data showed that free IPA-3, at concentrations of 5-30 μM, induced concentration-and time-dependent decreases in MTT staining with an IC50 between 10 and 35 μM, depending on the cell line. Interestingly, DU-145 cells were less susceptible to the toxicity of IPA-3 compared to PC-3 and LNCaP cells (FIGS. 1A-C). This difference was not a result of differences in media composition (FIGS. 1F-1H). Treatment of PC-3 cells with SSL-IPA-3 also decreased MTT staining. SSL-IPA-3 was not as toxic to these cells as free IPA-3 (FIGS. 1D-1E). Decreases in MTT staining were still detected at doses of 20 μM and higher in PC-3 cells. SSLIPA-3 was unable to induce significant decrease in MTT staining in DU-145 cells, even at the maximal encapsulation efficiency of 30 μM IPA-3. These data show that SSL-IPA-3 display anticancer activity in vitro.

Figure 2:
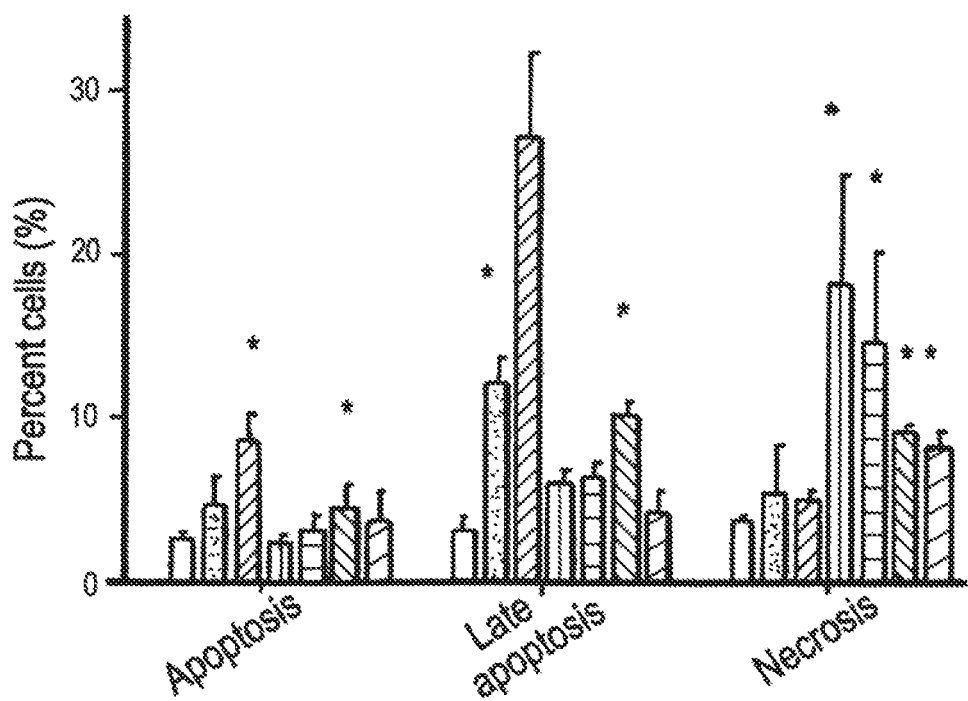
FIG. 2 is a bar graphs showing the quantification of cell death as determined by annexin V and PI staining in control, IPA-3 exposed, and SSL-IPA-3 exposed PC-3 cells after 48 hr. Annexin V and PI staining were determined using flow cytometry. Data are presented as the mean±SEM of the percent of cells in annexin V and PI staining as function of IPA-3 concentration; *p<0.05.

Annexin V and PI staining were assessed using flow cytometry to further study IPA-3 and SSL-IPA-3 induced death in PC-3 cells (FIG. 2). Treatment of cells with empty liposomes did not appreciably increase the percent cells staining positive either for annexin V alone or annexin and PI after 48 hr. In contrast, treatment with free IPA-3 (20-30 μM) significantly increased the percent of cell staining positive for annexin V alone, as well as those staining positive for both annexin V and PI, indicating the IPA-3 is inducing cell death via apoptosis. The increase in annexin V and PI staining were also time-dependent. SSLIPA-3 also increased the percent cells staining positive for annexin V alone, but appeared to have a greater effect on cells staining positive for both annexin V and PI. Further, SSL-IPA-3 also increased the number of cells staining positive for PI alone, suggesting that the presence of necrosis. The increase in cell staining positive for late apoptosis markers, as well as necrosis, suggest that the encapsulation of IPA-3 in liposomes enhanced cell death and may be more efficacious at killing tumor cell in vivo.

Figure 3A:
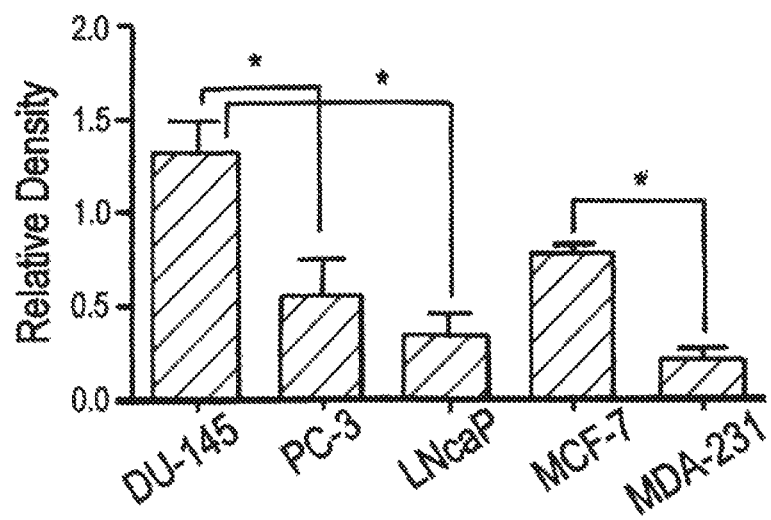
FIG. 3A is a histogram showing densitometry analysis of PAK-1 expression in different prostate and breast cancer cell lines as determined by immunoblot analysis (n=5).
Figure 3B:
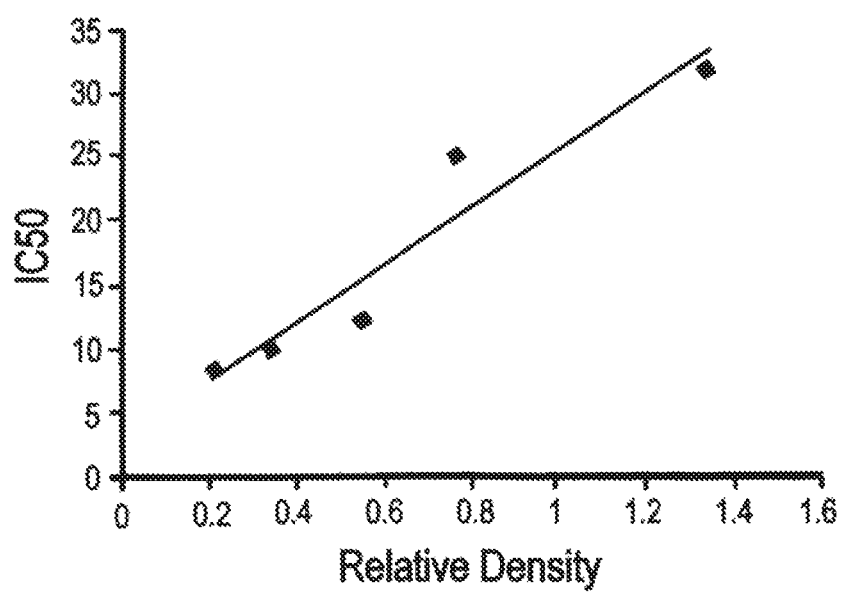
FIG. 3B is a plot showing correlation between PAK-1 expression and IC50 (µM) of PAK-1 inhibitor IPA-3 (n=3) (data presenting the linear correlation between PAK-1 expression and IPA-3 toxicity is shown in Table 3 below). Data are presented as the mean±SEM; *p<0.05.

To test whether the differential sensitivity of IPA-3 on DU-145 and PC-3 cells were due to the differences in the activity of PAK-1, PAK-1 protein expression was determined in PC-3, DU-145 and LNCaP cells, and compared to two breast cancer cell lines (MDA-231 and MCF-7). The results indicated that PAK-1 expression was variable in all cell lines tested, with higher levels being detected in DU-145 cells and the lowest level being detected in MDA-231 cells (FIGS. 3A). Comparison of the protein expression level of PAK-1 to the IC50 of free IPA-3 showed an excellent correlation with an $R^2$ of 0.92 (FIGS. 3B, Table 3). Cells with the highest levels of PAK-1 expression (DU-145 and MCF-7) had the highest IC50s (~32 and 25 μM, respectively), while cells with the lowest PAK-1 expression (MDA-231 and LNCaP cells) had the lowest IC50s (8 and 10 μM) respectively. These data indicate that differences in the sensitivity of cells to SSL-IPA-3 are mediated not by differences in sensitivity to the nanoparticles, but more so by differences in the expression of PAK-1.

TABLE 3

Comparison of the protein expression level of PAK-1 to the IC50 of free IPA-3

| Cell line | Relative Density | IC50(μM) |
|---|---|---|
| MDA-231 | 0.210882609 | 8 |
| LNcaP | 0.334556163 | 10 |
| PC-3 | 0.549933963 | 12 |
| MCF-7 | 0.761817712 | 25 |
| DU-145 | 1.336537272 | 32 |

Example 3

SSL-IPA-3 Inhibits the Prostate Tumor Xenograft Growth In Vivo

Materials and Methods

In Vivo Prostate Tumor Xenograft

All animal procedures listed in this article were performed as per the protocol approved by the Institutional Animal Care and Use Committee at the Charlie Norwood Veterans Affairs Medical Center, Augusta, GA (protocol #12-06-049).

PC-3 cells were grown to 60-70% confluent in 225-ml flasks. Next, cells were collected and suspended in sterile normal saline. Cell suspension (3 million cells//mouse) was injected subcutaneously (SC) in 6-8-weeks-old male athymic nude mice (Harlan, Indianapolis, IN) (n=5-6). All the treatments (DMSO, empty liposomes, free IPA-3 (5 mg/Kg), and SSL-IPA-3 (5 mg/kg) were started on day 7 from tumor implantation, and were administered two times a week (i.p.). Tumor diameters were measured with digital calipers on day 7, 14, 21, and 25, and the tumor volume in $mm^3$ were calculated by the modified ellipsoidal formula (Tumor volume=½[length×width$^2$]). Average size of the tumors prior to the treatment with free IPA-3 and SSL-IPA-3 were 42 $mm^3$. Mice were sacrificed on day 25 and tumors were dissected, weighed, and snap-frozen for further immunohistochemistry analysis.

TUNEL Assay

The TUNEL assay for in situ detection of apoptosis was performed using the ApopTag® Fluorescein in situ Apoptosis detection kit (Millipore, MA) as described previously8. Frozen sections taken from prostate tumor xenografts were fixed in 2% paraformaldehyde at 4° C. for 30 min. Fixed tissues were then permeabilized in (ethanol: acetic acid [2:1]) and labeled with fluorescein 12-dUTP using terminal deoxynucleotidyl transferase. Nuclei were counterstained with DAPI. Tissue sections were analyzed for apoptotic cells with localized green fluorescence using an inverted fluorescence microscope (Zeiss Axiovert100M, Carl Zeiss, Germany).

Results

Figure 4A:
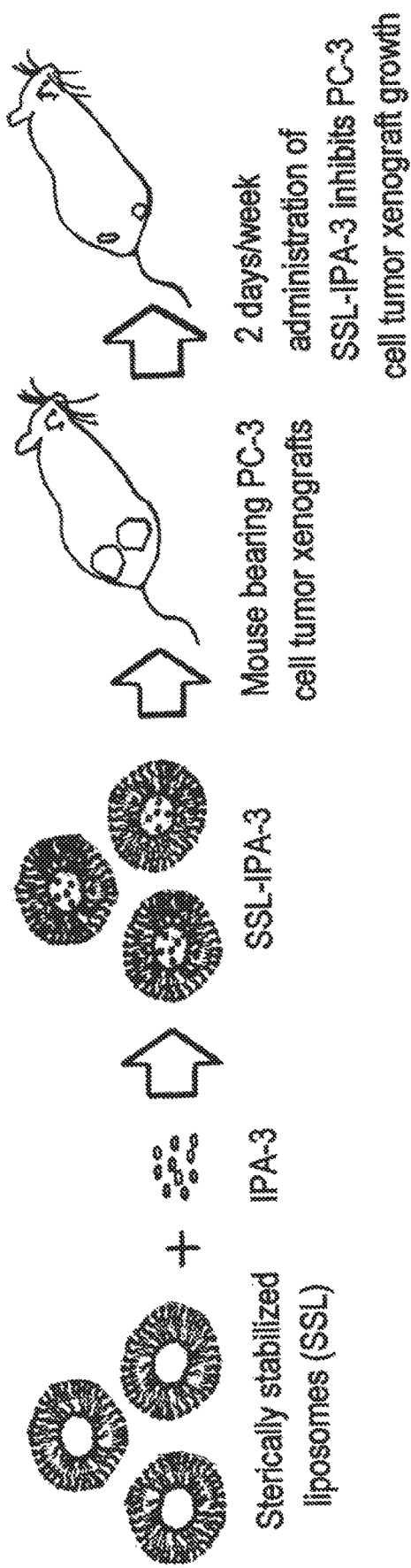
FIG. 4A is a schematic of an in vivo assay in which athymic nude mice bearing PC-3 cell tumor xenografts were treated with vehicle (DMSO), empty liposomes, IPA-3 or liposome encapsulated IPA-3 (SSL-IPA-3).
Figure 4B:
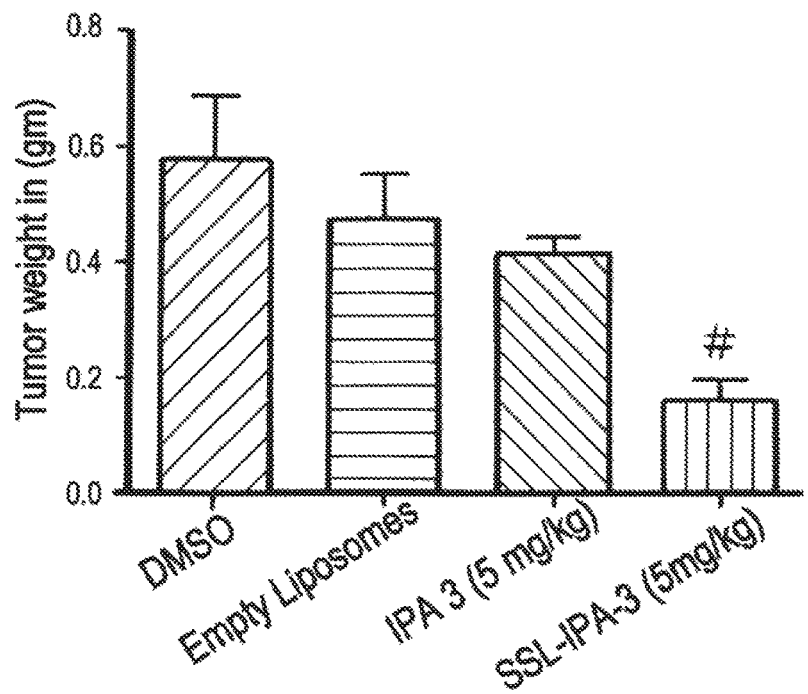
FIG. 4B is a histogram showing the weight of PC-3 cell tumor xenografts collected from athymic nude mice treated with vehicle (DMSO), empty liposomes, IPA-3 or liposome encapsulated IPA-3 on day 25 after tumor implantation and day 18 after the start of treatments (n=5-6).
Figure 4C:
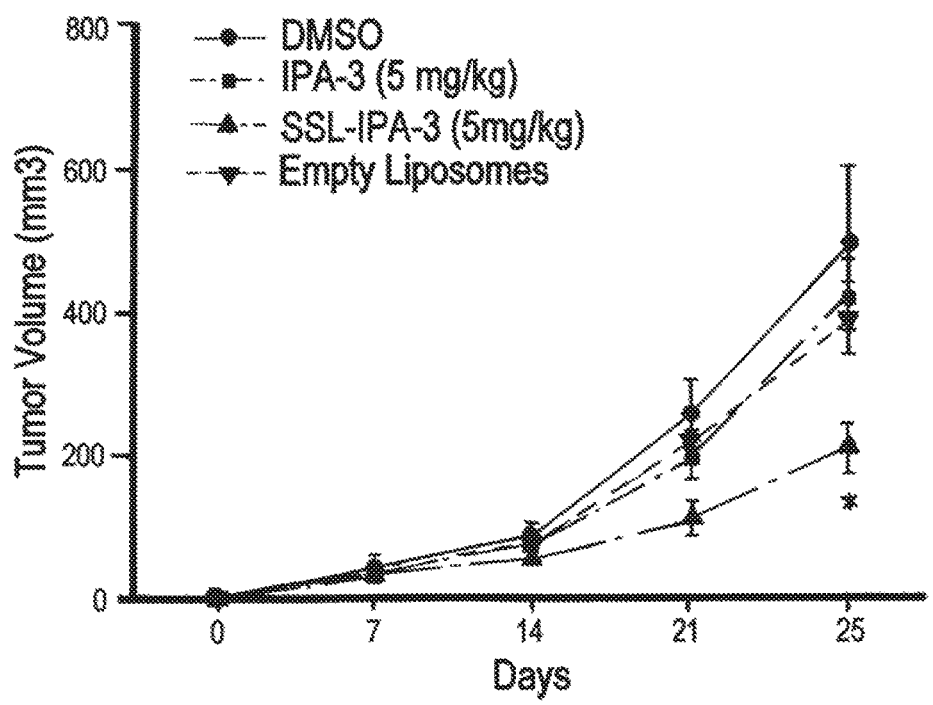
FIG. 4C is a bar graph showing the volume of PC-3 cell tumor xenografts on day 7, 14, 21 and 25 after implantation in athymic nude mice treated with vehicle (DMSO), empty liposomes, IPA-3 or liposome encapsulated IPA-3 as measured using calipers (n=5-6).
Figure 4D:
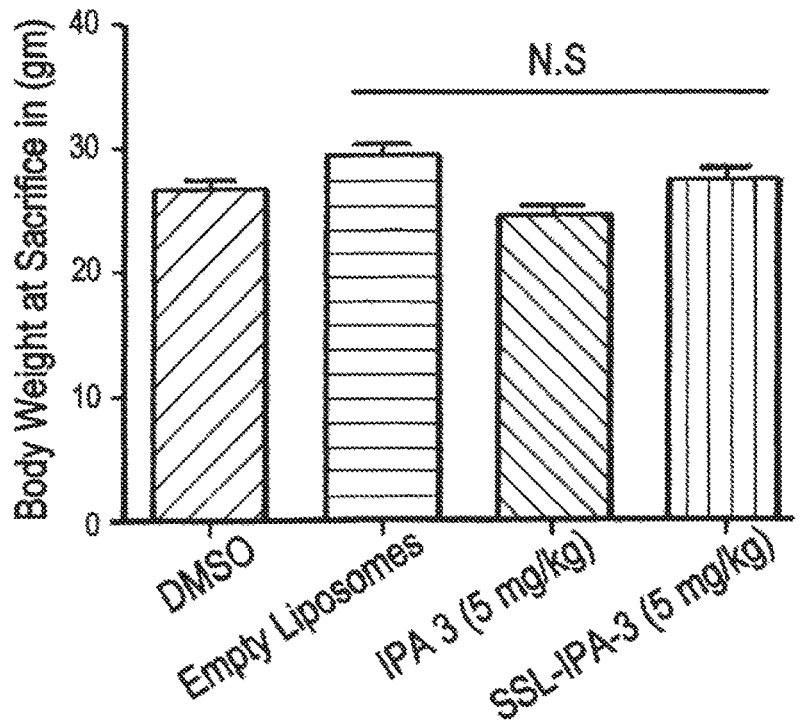
FIG. 4D is a histogram showing the body weight of the PC-3 cell tumor bearing athymic nude mice on day 25 after tumor implantation and day 18 after treatment with vehicle (DMSO), empty liposomes, IPA-3 or liposome encapsulated IPA-3. Data are presented as the mean±SEM; #p<0.01.

Inhibition of PAK-1 using IPA-3 reduced prostate tumor xenograft growth in athymic nude mice with daily administration (Al-Azayzih, et al., *Biochim Biophys Acta*. 2015; 1853: 1229-39.). An assay was designed to determine if 2 days/week administration of SSL-IPA-3 can inhibit the PC-3 cell tumor xenograft growth in vivo, compared to the same frequency of free IPA-3. The results indicated that 2 days/week administration of SSL-IPA-3 was indeed sufficient to inhibit the growth of PC-3 cell tumor xenografts, as compared to empty liposome and free IPA-3 administered groups (FIGS. 4A-4C). In fact, similar doses of free IPA-3 (2 days/week) administration did not have a significant effect on PC-3 tumor xenograft growth. There was no significant effect of empty liposome, free IPA-3 or SSL-IPA-3 administration on the body weight of mice even after 25 days (FIG. 4D). These data shows that SSL-IPA-3 is effective at inhibiting the growth of prostate tumor xenografts in vivo.

Figure 5:
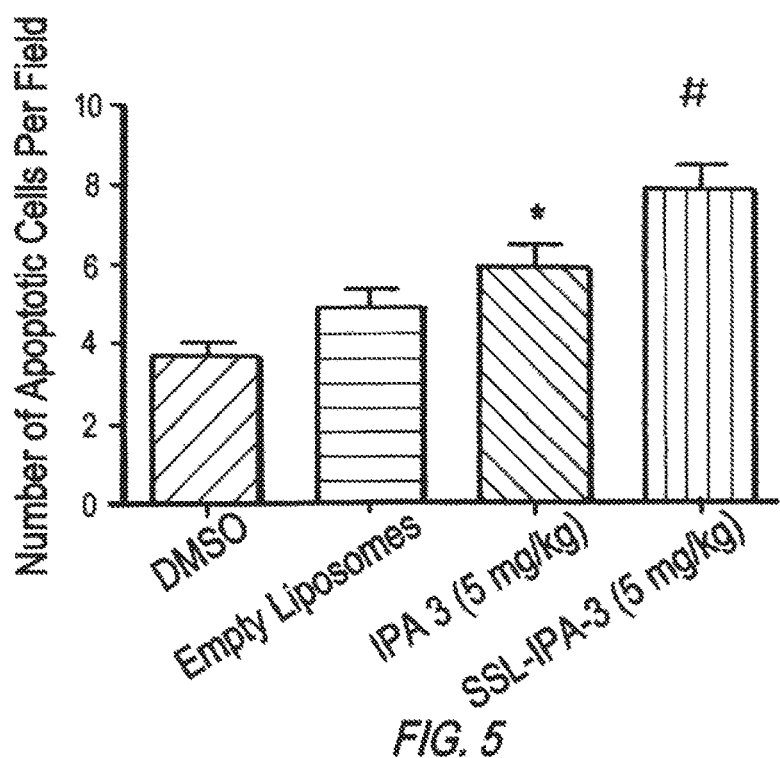
FIG. 5 is a histogram showing number of apoptotic (TUNEL positive) cells in PC-3 cell tumor xenograft sections from athymic nude mice treated with vehicle (DMSO), empty liposomes, IPA-3 or liposome encapsulated IPA-3 on day 25 after tumor implantation and day 18 after the start of treatments. (n=4). Data are presented as the mean±SEM; *p<0.05; #p<0.01.

The effect of SSL-IPA-3 and free IPA-3 on apoptosis in the PC-3 cell prostate tumor xenografts in vivo was tested using TUNEL staining. The results indicated that both SSL-IPA-3 and free IPA-3 treatments resulted in significant increases in the number of apoptotic cells per field compared to the control groups, but, the effect on the apoptosis was more greater in the SSL-IPA-3-treated group, as compared to the free IPA-3-treated group (FIG. 5). Thus, SSL-IPA-3's enhanced ability to limit prostate tumor growth in vivo correlates to increased apoptosis.

The Examples above show that IPA-3 was effectively and stably encapsulated in SSL. Analysis of zeta potential and size indicated that these nanoparticles would be functional for clinical application, and the activity of these formulations were verified in vitro. SSL-IPA-3 were not as effective as free IPA-3 in vitro and in vivo, as this is commonly seen in many studies (Zhu, et al., *J Pharm Sci*. 2011; 100: 3146-59; Mock, et al., *Integr Biol* (Camb). 2013; 5: 172-82; Quach, et al., *Mol Pharm*. 2014; 11: 3443-51). However, the effect of SSL-IPA-3 was shown to be cell type-dependent and mediated by the level of expression of PAK-1. The decreased susceptibility of DU-145 cells to SSL-IPA-3 liposomes indeed mirrored their decreased susceptibility to free IPA-3. These differences were not a result of difference in sensitivity to the formulation used as DU-145 and PC-3 cells were equally sensitive to another anti-cancer drug, doxorubicin, encapsulated in SSL and a modified liposome formulation (Mock, et al., *Integr Biol* (Camb). 2013; 5: 172-82; Zhu, et al., *J Pharm Sci*. 2011; 100: 3146-59). The in vitro studies also revealed that free IPA-3 displays greater anti-tumor activity than SSL-IPA-3. Encapsulated IPA-3 in SSL must first be released from the liposomes before acting on its target PAK-1. These data also indicate that the therapeutic efficacy of SSL-IPA-3 may be limited in cancers that express high levels of PAK-1. It is also possible that the differential expression of PAKs in these cancers may also mitigate the toxicity.

Biophysical characterization of SSL-IPA-3 showed excellent stability, as based on the maintenance of zeta potential, size and IPA-3 levels for at least 7 days. Because of its lipophilicity, IPA-3 is probably mostly incorporated in the phospholipid bilayer of the liposomes, which provides a hydrophobic environment. Once trapped, IPA-3 may remain in the liposomal bilayer due to their lower affinity for the inner and outer aqueous regions of the liposomes (Allen, et al., *Drugs*. 1998; 56: 747-56; Immordino, et al., *International journal of nanomedicine*. 2006; 1: 297-315). However, given enough time, IPA-3 may dissociate from the SSL. This may be the cause for the decrease in IPA-3 levels seen in these formulations after 14 days. Nevertheless, the results show that SSL-IPA-3 is reasonably stable and therapeutically active, even in biological fluids. Lyophilization is a promising approach to ensure the extension of shelf-life and longer-term stability of liposomes. Thus, methods such as water replacement and vitrification could also be used to produce an extended shelf-life (Chen, et al., *Journal of controlled release: official journal of the Controlled Release Society*. 2010; 142: 299-311).

The results also show that 2 days/week administration of SSL-IPA-3 is effective in decreasing the growth of human prostate cells in vitro and tumor (PC-3) xenografts in vivo. Further, the data showed enhanced efficacy of SSL-IPA-3 compared to free IPA-3, which indicates that the activity of SSL-IPA-3 becomes more effective in an in vivo environment. The increase in efficacy of the SSL-IPA-3, as compared to free IPA-3, is believed to be at least in-part because the encapsulation of IPA-3 in SSL extends the half-life of IPA-3 and overcomes its rapid metabolism in its free form. The implications of these findings are significant because they indicate decreased dosing, with higher efficacy, which could decrease side-effects and other off-target toxicities associated with anti-cancer agents. Although the experiments in this study are focused on the activity of SSL-IPA-3 on prostate cancer, this targeting strategy can additionally be used to target other cancers such as breast cancer as was shown by the in vitro studies.

In conclusion, the exemplified SSL-based nanoparticle formulation is reasonably stable and shows excellent efficacy both in vitro and in vivo. These data indicate that SSL-IPA-3 is an effective targeting strategy for inhibiting prostate cancer growth. Data in this study also indicate that the activity of IPA-3 is cell dependent and is mediated by the level of expression of PAK-1 in cancer cells.

We claim:

1. A nanoparticulate composition comprising a p21 activated kinase (PAK) inhibitor and a lipid-based delivery vehicle, wherein the p21 activated kinase (PAK) inhibitor is Inhibitor targeting P21-activated kinase-1 (PAK1) activation-3 (IPA-3), a prodrug, or a pharmaceutically acceptable salt thereof, and wherein the lipid-based delivery vehicle is a liposome which consists essentially of: (1) 1, 2-distearoyl-sn-glycero-3-phosphatidylcholine (DSPC) and/or 1, 2-distearoyl -sn-glycero-3-phosphatidylethanolamine (DSPE); (2) at least one pegylated lipid; and (3) cholesterol.

2. The nanoparticulate composition of claim 1, wherein the at least one pegylated lipid is pegylated 1, 2-distearoyl-sn-glycero-3-phosphatidylethanolamine (DSPE).

3. The nanoparticulate composition of claim 1, wherein the liposome is a sterically-stabilized liposome.

4. The nanoparticulate composition of claim 1, having a polydispersity index (PDI) of about 0.05 to about 0.139, a zeta potential of about -28.1v, or a combination thereof.

5. The nanoparticulate composition of claim 1, having a diameter of about 75 nm to about 500 nm.

6. The nanoparticulate composition of claim 1, wherein the at least one pegylated lipid is DSPE-PEG2000.

7. The nanoparticlate composition of claim 1, wherein the ratio of DSPC and/or DSPE, at least one pegylated lipid, and cholesterol is 9:1:5.

8. The nanoparticulate composition of claim 1, wherein the PAK-1 inhibitor is Inhibitor targeting P21-activated kinase-1 (PAK1) activation-3 (IPA-3) or pharmaceutically acceptable salt thereof.

9. The nanoparticulate composition of claim 8 wherein the PAK-1 inhibitor is IPA-3.

10. A pharmaceutical composition comprising the nanoparticulate composition of claim 1 and a pharmaceutically acceptable carrier.

11. A dosage unit comprising the composition of claim 10 in an effective amount to treat cancer in a subject in need thereof for 2 to 5 days.

12. A method of treating cancer comprising administering a subject in need thereof the pharmaceutical composition of claim 10 in an effective amount to treat cancer.

13. The method of claim 12, wherein the cancer comprises cancer cells that express PAK-1 at a higher expression level than normal cells of the same type.

14. The method of claim 12, wherein the cancer is prostate cancer or breast cancer.

15. The method of claim 12, wherein the pharmaceutical composition is administered to the subject between 1 and 3 times per week.

16. The method of claim 15, wherein the pharmaceutical composition is administered 2 times per week.

17. A method of treating prostate cancer comprising administering a subject with prostate cancer an effective amount of the dosage unit of claim 11 to treat the subject for 2-5 days.

18. The nanoparticulate composition of claim 1, wherein the lipid-based delivery vehicle is a liposome which consists of: (1) 1, 2-distearoyl-sn -glycero-3-phosphatidylcholine (DSPC) and/or 1, 2-distearoyl-sn-glycero-3-phosphatidylethanolamine (DSPE); (2) at least one pegylated lipid; and (3) cholesterol.

19. The nanoparticulate composition of claim 18, wherein the at least one pegylated lipid is pegylated 1, 2-distearoyl-sn-glycero -3-phosphatidylethanolamine (DSPE).

20. The nanoparticulate composition of claim 18, wherein the liposome is a sterically-stabilized liposome.

* * * * *

UNITED STATES PATENT AND TRADEMARK OFFICE
CERTIFICATE OF CORRECTION

PATENT NO. : 11,969,396 B2
APPLICATION NO. : 18/047915
DATED : April 30, 2024
INVENTOR(S) : Somanath Rammohan Shenoy, Brian S. Cummings and Wided Najahi-Missaoui It is certified that error appears in the above-identified patent and that said Letters Patent is hereby corrected as shown below:

In the Specification

Column 1, Lines 18-22, replace the following paragraph:
"This invention was made with government support under grant number W81XWH-16-1-0611 and W81XH-16-1-0612 awarded by the U.S. Army Medical Research (DODAMR). The government has certain rights in the invention. (37 CFR § 401.14 f (4))."

With the following paragraph:
--This invention was made with government support under W81XWH-16-1-0612, and W81XWH-16-1-0611 awarded by the Defense Health Agency, Medical Research and Development Branch. The government has certain rights in the invention.--

Signed and Sealed this
Tenth Day of September, 2024

*Katherine Kelly Vidal*

Katherine Kelly Vidal
*Director of the United States Patent and Trademark Office*